US008241664B2

(12) United States Patent
Dudley et al.

(10) Patent No.: US 8,241,664 B2
(45) Date of Patent: Aug. 14, 2012

(54) PHARMACEUTICAL DELIVERY SYSTEMS FOR HYDROPHOBIC DRUGS AND COMPOSITIONS COMPRISING SAME

(75) Inventors: Robert E. Dudley, Rosemary Beach, IL (US); Panayiotis P. Constantinides, Gurnee, IL (US)

(73) Assignee: Clarus Therapeutics, Inc, Northbrook, IL (US)

( * ) Notice: Subject to any disclaimer, the term of this patent is extended or adjusted under 35 U.S.C. 154(b) by 1080 days.

(21) Appl. No.: 11/911,446

(22) PCT Filed: Apr. 14, 2006

(86) PCT No.: PCT/US2006/014207
§ 371 (c)(1),
(2), (4) Date: Nov. 12, 2007

(87) PCT Pub. No.: WO2006/113505
PCT Pub. Date: Oct. 26, 2006

(65) Prior Publication Data
US 2008/0317844 A1    Dec. 25, 2008

Related U.S. Application Data

(60) Provisional application No. 60/671,454, filed on Apr. 15, 2005, provisional application No. 60/721,971, filed on Sep. 30, 2005.

(51) Int. Cl.
*A61K 9/64* (2006.01)
*A61K 31/56* (2006.01)
*A01N 45/00* (2006.01)

(52) U.S. Cl. ......... 424/456; 514/170; 514/171; 514/179

(58) Field of Classification Search .................. None
See application file for complete search history.

(56) References Cited

U.S. PATENT DOCUMENTS

| | | | |
|---|---|---|---|
| 3,164,520 A * | 1/1965 | Huber ........................ 514/174 |
| 3,266,991 A | 8/1966 | Wettstein et al. |
| 4,147,783 A | 4/1979 | van der Vies |
| 4,572,915 A | 2/1986 | Crooks |
| 4,719,239 A | 1/1988 | Muller et al. |
| 5,342,625 A | 8/1994 | Hauer et al. |
| 5,645,856 A | 7/1997 | Lacy et al. |
| 5,891,469 A | 4/1999 | Amselem |
| 6,013,665 A | 1/2000 | DeMichele et al. |
| 6,096,338 A | 8/2000 | Lacy et al. |
| 6,160,007 A | 12/2000 | DeMichele et al. |
| 6,248,363 B1 | 6/2001 | Patel et al. |
| 6,267,985 B1 | 7/2001 | Chen et al. |
| 6,294,192 B1 | 9/2001 | Patel et al. |
| 6,309,663 B1 | 10/2001 | Patel et al. |
| 6,383,471 B1 | 5/2002 | Chen et al. |
| 6,451,339 B2 | 9/2002 | Patel et al. |
| 6,458,383 B2 | 10/2002 | Chen et al. |
| 6,569,463 B2 | 5/2003 | Patel et al. |
| 6,652,880 B1 | 11/2003 | Aylwin et al. |
| 6,665,880 B2 | 12/2003 | Poppe |
| 6,761,903 B2 | 7/2004 | Chen et al. |
| 6,923,988 B2 | 8/2005 | Patel et al. |
| 6,982,281 B1 | 1/2006 | Chen et al. |
| 7,025,979 B2 | 4/2006 | Neischlag et al. |
| 7,374,779 B2 | 5/2008 | Chen et al. |
| 2001/0018069 A1 | 8/2001 | Johnson et al. |
| 2002/0068693 A1 | 6/2002 | Jeng et al. |
| 2003/0022875 A1 | 1/2003 | Wilson et al. |
| 2003/0104048 A1 | 6/2003 | Patel et al. |
| 2003/0180352 A1 | 9/2003 | Patel et al. |
| 2003/0181431 A1 * | 9/2003 | Hodgen ........................ 514/171 |
| 2003/0186892 A1 | 10/2003 | Taneja |
| 2003/0235595 A1 | 12/2003 | Chen et al. |
| 2003/0236236 A1 | 12/2003 | Chen et al. |
| 2004/0002445 A1 | 1/2004 | Taneja |
| 2004/0127476 A1 | 7/2004 | Kershman et al. |
| 2005/0032762 A1 * | 2/2005 | Hubler et al. .................. 514/178 |
| 2005/0096296 A1 | 5/2005 | Fikstad et al. |
| 2005/0096365 A1 | 5/2005 | Fikstad et al. |
| 2005/0171193 A1 | 8/2005 | Chen et al. |
| 2005/0176692 A1 * | 8/2005 | Amory et al. .................. 514/171 |
| 2005/0287203 A1 | 12/2005 | Nijs De et al. |
| 2006/0003002 A1 | 1/2006 | Fikstad et al. |
| 2006/0034937 A1 | 2/2006 | Patel |
| 2007/0232548 A1 | 10/2007 | Taneja |
| 2008/0020053 A1 | 1/2008 | Persson et al. |
| 2008/0217692 A1 | 9/2008 | Anderson et al. |
| 2008/0317844 A1 | 12/2008 | Dudley et al. |
| 2008/0317850 A1 | 12/2008 | Hewitt et al. |
| 2009/0074859 A1 | 3/2009 | Patel |

FOREIGN PATENT DOCUMENTS

EP    0 904 064 B1    10/2001
(Continued)

OTHER PUBLICATIONS

International Search Report and Written Opinion mailed Dec. 1, 2010, in International Application No. PCT/US2010/030788.
S. Yu. Kalinchenko "Testosteron-korol' gormonov I gormon korolei". The Journal "Sex and Life", 2004, pp. 12-22 / online [retrieved on Mar. 26, 2010 13:27]. Retrieved from the Internet: URL:http://www.lazmed.ru/interesting/publications/testosteron.html. (partial translation only).
A.T. Burbello at al., Sovremennye lekarstvennyesredstva S-Pb "Neva", 2004, p. 567. (partial translation only).
Noguchi, T, et al, "The effect of drug lipophilicity and lipid vehicles on the lymphatic absorption of various testosterone," International Journal of Pharmaceutics, 24 (1985) 173-184, May 5, 2012.
MacGregor, KJ, et al, "Influence of lipolysis on drug absorption from the gastro-intestinal tract," Advanced Drug Delivery Reviews 25 (1997) 33-46.
Tenover, JL, The Androgen-Deficient Aging Male: Current Treatment Options, Reviews in Urology, 2003, vol. 5, Suppl 1, S22-S28.

(Continued)

*Primary Examiner* — Anne Gussow
*Assistant Examiner* — Thurman Wheeler
(74) *Attorney, Agent, or Firm* — Dennis A. Bennett; Brock Levin

(57) ABSTRACT

A drug delivery system for oral administration of hydrophobic drugs with enhanced and extended absorption and improved pharmacokinetics is provided. In one embodiment, formulations comprising testosterone and testosterone esters, e.g., testosterone palmitate, are disclosed. Methods of treating a hormone deficiency or effecting male contraception with the inventive formulations are also provided.

59 Claims, 15 Drawing Sheets

FOREIGN PATENT DOCUMENTS

| | | |
|---|---|---|
| GB | 1 264 677 | 2/1972 |
| GB | 2 228 198 A | 8/1990 |
| WO | WO 92/18147 | 10/1992 |
| WO | WO 93/02664 | 2/1993 |
| WO | WO 94/08610 | 4/1994 |
| WO | WO9524893 * | 9/1995 |
| WO | WO 97/40823 | 11/1997 |
| WO | 00/59512 A1 | 10/2000 |
| WO | WO 2006/013369 A2 | 2/2006 |
| WO | WO 2006/113505 A2 | 10/2006 |

OTHER PUBLICATIONS

Addo et al., "Non-polar extracts of serum from males contain covert radioimmunoassayable testosterone," [on line] (abstract, database PubMed PMID: 2588302] [found Nov. 19, 2009]), Sep. 1989, pp. 257-269, vol. 54, No. 3.

Constantinides, P., "Lipid Microemulsions for Improving Drug Dissolution and Oral Absorption: Physical and Biopharmaceutical Aspects," Pharmaceutical Research, 1995, pp. 1561-1572, vol. 12, No. 11.

Graham-Smith et al., "The Oxford Reference-book on Clinical Pharmacology and Pharmacotherapy", M. Meditsina Publishers, 2000, pp. 25, 136-137 (partial translation).

Maisey et al., "Clinical Efficacy of Testosterone Undecanoate in Male Hypogonadism," Clinical Endocrinology, 1981, pp. 625-629, vol. 14.

S. Yu. Kalinchenko "Testosteron-korol' gormonov I gormon korolei". The Journal "Sex and Life", 2004, pp. 12-22 / online [retrieved on Mar. 26, 2010 13:27]. Retrieved from the Internet: URL:http://www.lazmed.ru/interesting/publications/testosteron.html.

A.T. Burbello et al., Sovremennye lekarstvennyesredstva S-Pb "Neva", 2004, p. 567.

Andriol® Testocaps™ Consumer Medicine Information, Sep. 2003.

Tso, et al. "Intestinal Absorption and Lymphatic Transport of a High γ-Linolenic Acid Canola Oil in Lymph Fistula Sprague-Dawley Rats", American Society for Nutritional Sciences, 2002, pp. 218-221.

* cited by examiner

PHARMACEUTICAL DELIVERY SYSTEMS FOR HYDROPHOBIC DRUGS AND COMPOSITIONS COMPRISING SAME

CLAIM OF PRIORITY

This application claims priority to U.S. provisional application Nos. 60/671,454 filed Apr. 15, 2005 and 60/721,971 filed Sep. 30, 2005, both of which disclosures have been incorporated by reference herein in their entirety.

FIELD OF THE INVENTION

The present invention relates generally to pharmaceutical delivery systems of hydrophobic drugs and compositions comprising same. More particularly, the present invention relates to pharmaceutical compositions comprising testosterone and esters thereof with enhanced and extended absorption and pharmacokinetics.

BACKGROUND OF THE INVENTION

Many pharmaceutically active compounds intended for oral administration are poorly soluble in water providing a challenge to formulate these drugs in a drug delivery system that exhibits the desirable pharmacokinetic profiles in vivo. Poor oral bioavailability may lead to ineffective therapy, the need for higher dosing and/or undesirable side effects. As well, pharmaceutical preparations with relatively short half-lives require frequent dosing at the expense of patient inconvenience and higher therapy costs.

Sex hormones (e.g., testosterone and its esters) are marginally water soluble, and attempts have been made to increase their bioavailability, particularly when taken orally. However, administration of testosterone, per se, presents additional challenges. Indeed, while testosterone given by mouth is essentially completely absorbed into the portal circulation, because of extensive first-pass hepatic metabolism, the serum concentration of testosterone following this route of administration is low unless very large doses are administered. To overcome this problem, attempts have been made to alkylate testosterone at the C-17 position (e.g., with a methyl group to form methyltestosterone) thereby reducing metabolism by the liver. Unfortunately, however, mere alkylation of testosterone has not yielded desirable bioavailability and has been associated with potentially serious hepatotoxicity.

Other attempts have managed to increase the transient bioavailability of testosterone and its derivatives with lipophilic solvents and surfactants. Nonetheless, even in cases where bioavailability was enhanced, the delivery systems failed to maintain desirable serum concentrations over an extended period of time.

Accordingly, there is a need for a drug delivery system that can provide enhanced bioavailability of hydrophobic drugs in vivo. In addition, with respect to testosterone therapy, there is a need for an oral drug delivery system that may provide enhanced bioavailability of testosterone and/or an ester thereof in vivo over an extended period of time.

SUMMARY OF THE INVENTION

In one embodiment of the present invention, a pharmaceutical composition is provided comprising testosterone palmitate (TP), or a testosterone ester thereof, and two or more lipid components at least the first of which comprises a hydrophilic surfactant and at least the second of which comprises a lipophilic surfactant that provides for the controlled release of TP, said lipid components together providing for the solubilization of TP. The pharmaceutical composition may further comprise at least three lipid components at least the first of which comprises a hydrophilic surfactant, at least the second of which comprises a lipophilic surfactant that provides for the controlled release of TP and at least the third of which comprises a lipophilic surfactant that further provides for the solubilization of TP. As well, the pharmaceutical composition may further comprise a second lipid-soluble therapeutic agent, such as a synthetic progestin. Formulations comprising same may be preferably in the form of an orally active male contraceptive.

The first lipid component may exhibit an HLB of 10 to 45, preferably 10 to 30, and more preferably 10 to 20. The second lipid component may exhibit an HLB of less than about 10, preferably less than about 7, and more preferably less than about 5. Further, the second lipid component may exhibit a melting point in the range of about 25° C. to about 80° C., preferably about 35° C. to about 65° C., and more preferably about 40° C. to about 60° C. The second lipid component may be chosen from the group consisting of stearic acid, palmitic acid, glycerol and PEG esters thereof, Precirol ATO 5 and Gelucires.

In some embodiments, the lipophilic surfactant further comprises a "sustained" or controlled-release" surfactant which may be chosen from the group consisting of stearic acid, palmitic acid, glycerol and PEG esters thereof, Precirol AT05, Imwitor 191, Myverol 18-06, Imwitor 370, Imwitor 375, Caprol ET, Cithrol 2MS, Marosol 183 and combinations thereof. The hydrophilic surfactant may be a poloxyl derivative of castor oil. Commercially available products of this class are supplied under the tradenames, Cremophor or Etocas and include, Cremophor EL and RH 40 and Etocas 35 and 40. Chemophor, RH40 or Etocas 40 are preferred.

Compositions of the present invention may comprise, based on weight, 10-70% a lipophilic surfactant; 1-40% a controlled release surfactant; and 5-60% a hydrophilic surfactant; and preferably 30-50% a lipophilic surfactant; 5-25% a controlled release surfactant; and 30-40% a hydrophilic surfactant. The compositions further comprise about 5 to about 50 percent, by weight, testosterone palmitate, preferably, about 20 to about 40 percent, by weight, testosterone palmitate. The inventive pharmaceutical compositions may also comprise one or more cosolvents and/or filled into a hard or soft gelatin capsule.

In another aspect of the present invention, a method of preventing or alleviating the symptoms of testosterone deficiency in a mammalian subject is provided comprising administering to the mammalian subject an effective amount of testosterone palmitate (TP) solubilized in two or more lipid components, such that the administration of said solubilized TP raises the mammalian subject's steady state serum level of testosterone to within those levels found in mammalian subjects having no testosterone deficiency and providing at least some relief from such symptoms. In human males, the administering is preferably once or twice daily and the mammal's steady state serum level of testosterone is raised to fall within a range of about 300 ng/dl to about 1100 ng/dl. With human females, a similar dosing schedule (with a lower daily TP dose) is preferred to achieve serum testosterone levels of approximately 10 to 100 ng/dl. In some embodiments, the method may raise the mammal's steady state serum level of testosterone by 150%, 200%, 300% or 400%. The method may further comprise administering an amount of a synthetic progestin sufficient to inhibit gonadotropin release in said mammalian subject and produce severe oligospermia or azospermia.

In yet another aspect of the present invention, a method of delivering steady-state serum levels of testosterone effective to provide at least some relief from symptoms of testosterone deficiency is provided comprising solubilizing testosterone palmitate (TP) in two or more lipid components at least the first of which comprises a hydrophilic surfactant and at least the second of which comprises a lipophilic surfactant that provides for the controlled release of TP and administering an effective amount of the solubilized TP to a subject suffering from the symptoms of testosterone deficiency. The method can further comprise solubilizing TP in at least three lipid components at least the first of which comprises a hydrophilic surfactant, at least the second of which comprises a lipophilic surfactant that provides for the controlled release of TP and at least the third of which comprises a lipophilic surfactant that further provides for the solubilization of TP.

In further yet another aspect of the present invention, a method of providing extended release of testosterone in vivo is provided, the method comprising solubilizing testosterone palmitate (TP) in a lipid mixture comprising two or more lipid components at least the first of which comprises a hydrophilic surfactant and at least the second of which comprises a lipophilic surfactant having a melting point of greater than about 35° C.

In still further yet another embodiment of the present invention, a pharmaceutical composition is provided comprising testosterone palmitate (TP) and two or more lipid components at least the first of which comprises a hydrophilic surfactant and at least the second of which comprises a lipophilic surfactant, in which the at least first hydrophilic component or the at least second lipophilic component provides for the controlled release of TP, and said lipid components together provide for the solubilization of TP. In one embodiment, the at least first hydrophilic component provides for the controlled release of TP.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. For example, some embodiments of the invention may combine TP with other active drugs, including hormonals, in an oral delivery system that, in part, prevents or alleviates symptoms associated with testosterone deficiency. It is important, therefore, that the claims be regarded as including such equivalent constructions insofar as they do not depart from the spirit and scope of the present invention.

DETAILED DESCRIPTION OF THE INVENTION

Figure 1:
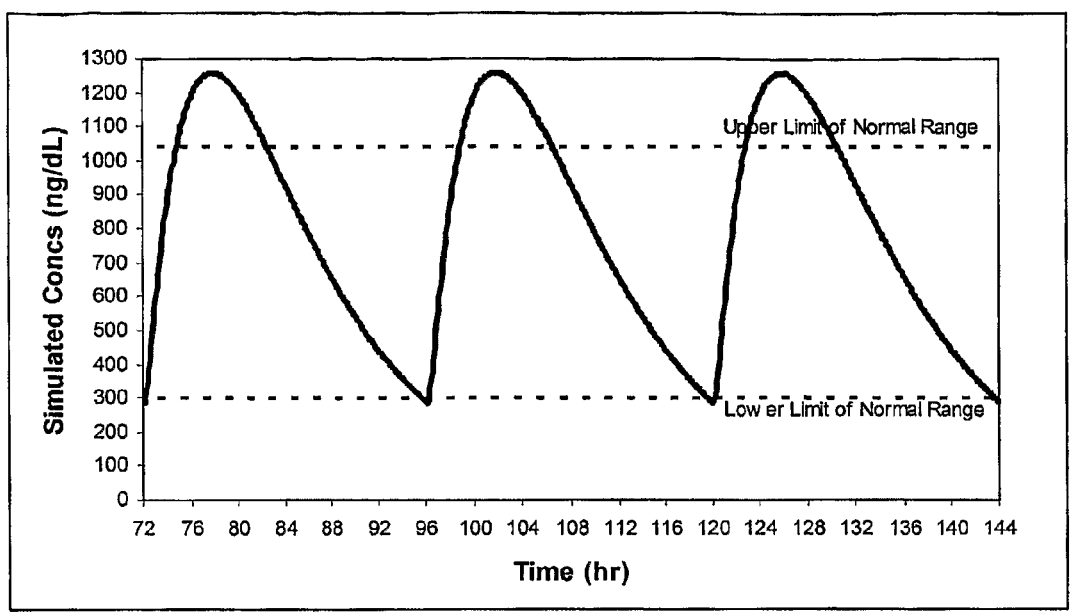
FIG. 1 depicts a steady-state pharmacokinetic profile of the serum concentration of testosterone upon ingestion of a formulation of TP, which maximizes diurnal variation while producing an early Tmax, preferably compatible with early morning, once-daily dosing.
Figure 2:
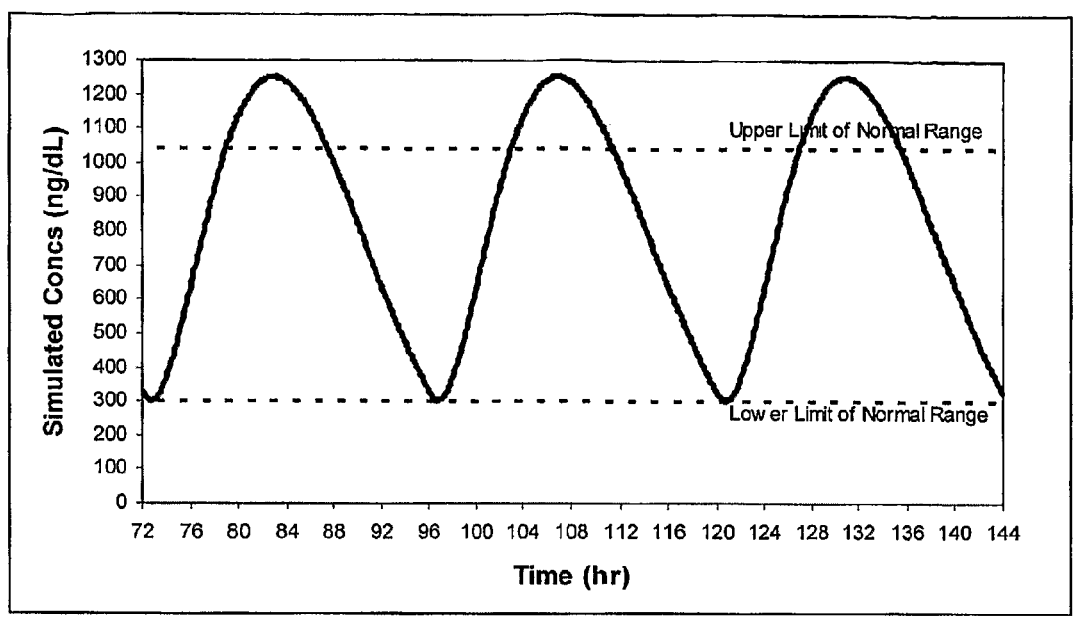
FIG. 2 depicts a steady-state pharmacokinetic profile of the serum concentration of testosterone upon ingestion of a formulation of TP which maximizes diurnal variation while producing a late Tmax, preferably compatible with nighttime, once-daily dosing.
Figure 3:
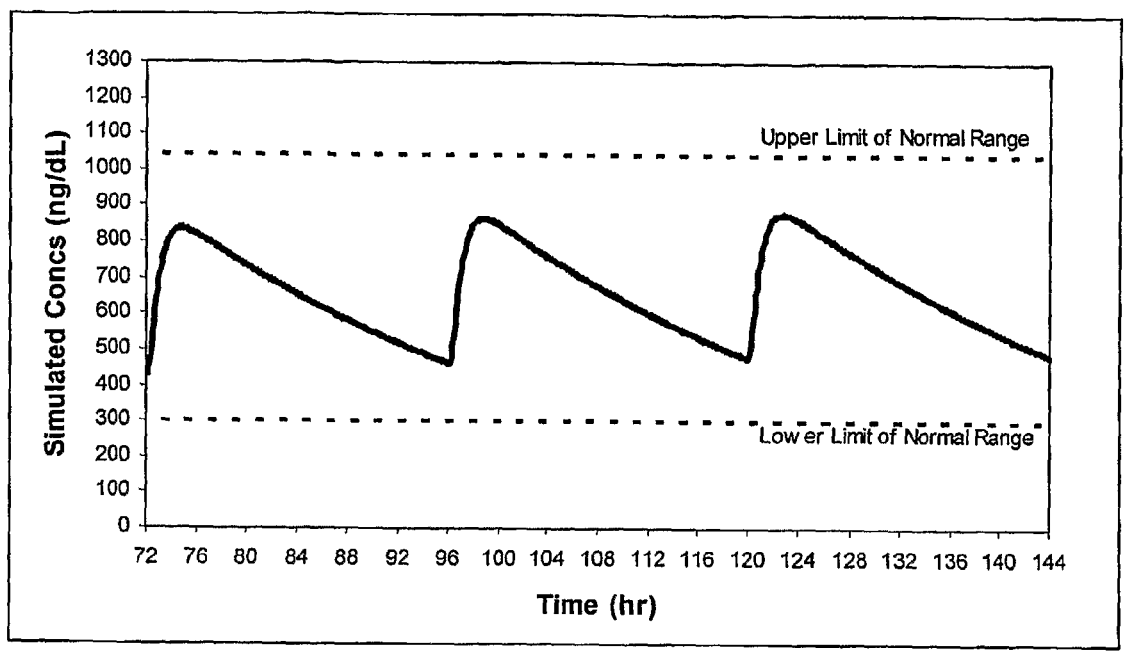
FIG. 3 depicts a steady-state pharmacokinetic profile of the serum concentration of testosterone upon ingestion of a formulation of TP which provides physiological diurnal variation and an early Tmax, preferably compatible with early morning, once-daily dosing.
Figure 4:
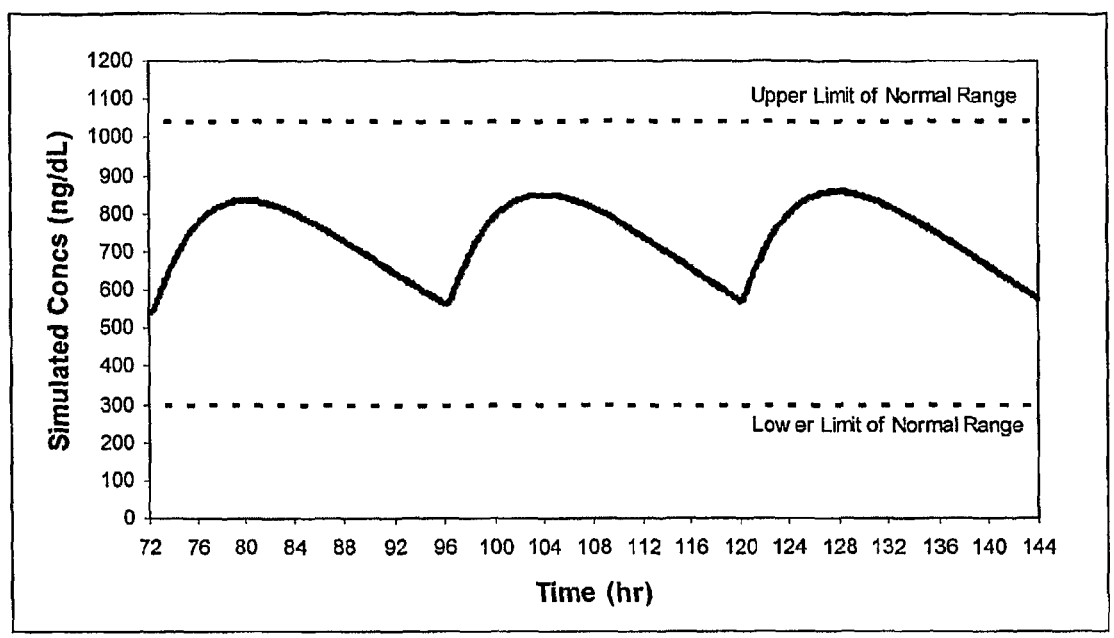
FIG. 4 depicts a steady-state pharmacokinetic profile of the serum concentration of testosterone upon ingestion of a formulation of TP, which provides physiological diurnal variation and a delayed Tmax, preferably compatible with early morning, once-daily dosing.
Figure 5:
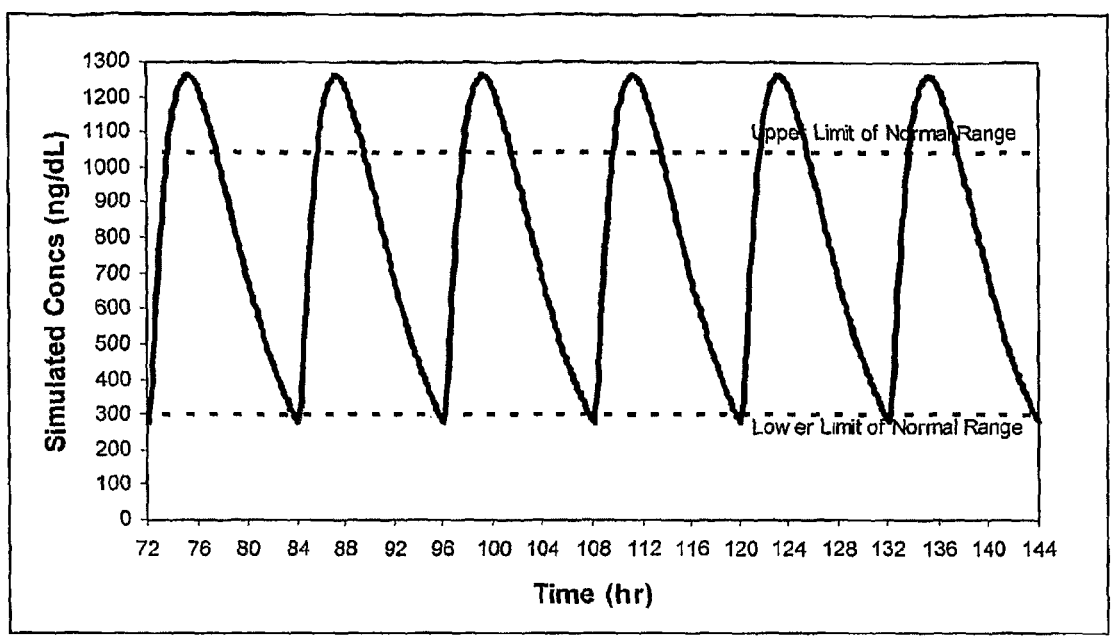
FIG. 5 depicts a steady-state pharmacokinetic profile of the serum concentration of testosterone upon ingestion of a formulation of TP, which provides a short elimination half-life and an early Tmax, preferably compatible with maximal patient activity soon after waking and twice-daily dosing.
Figure 6:
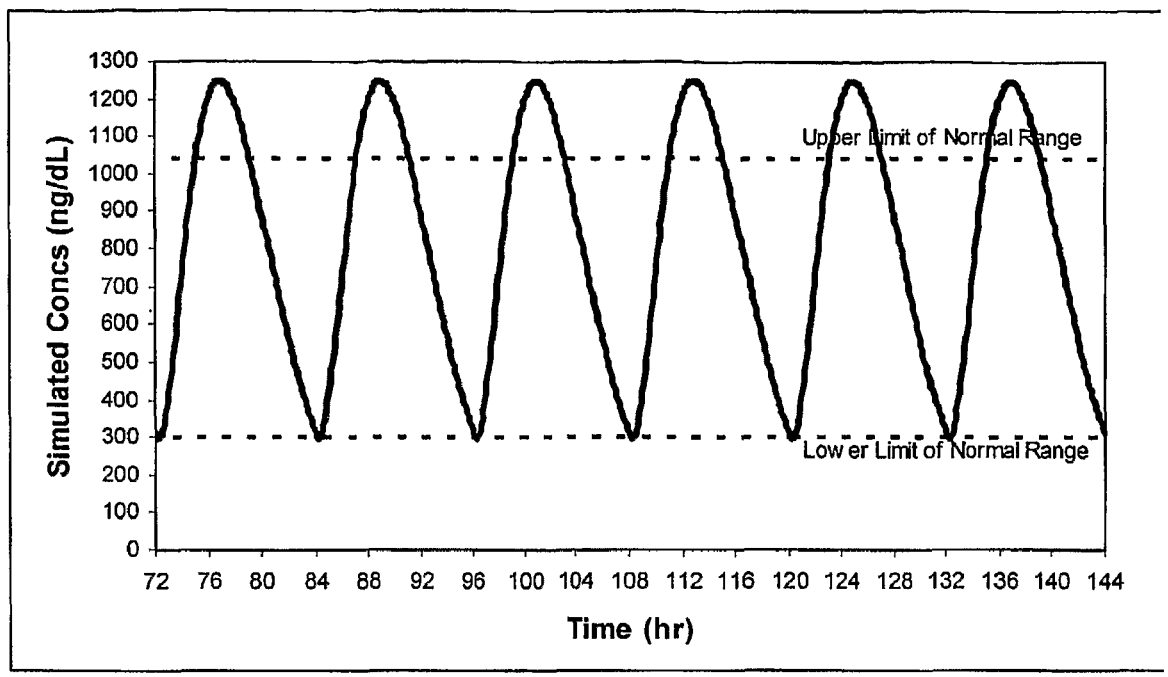
FIG. 6 depicts a steady-state pharmacokinetic profile of the serum concentration of testosterone upon ingestion of a formulation of TP, which provides a relatively short elimination half-life and a delayed Tmax with maximal activity about waking time. One of the twice-daily doses is preferably scheduled before bedtime.
Figure 7:
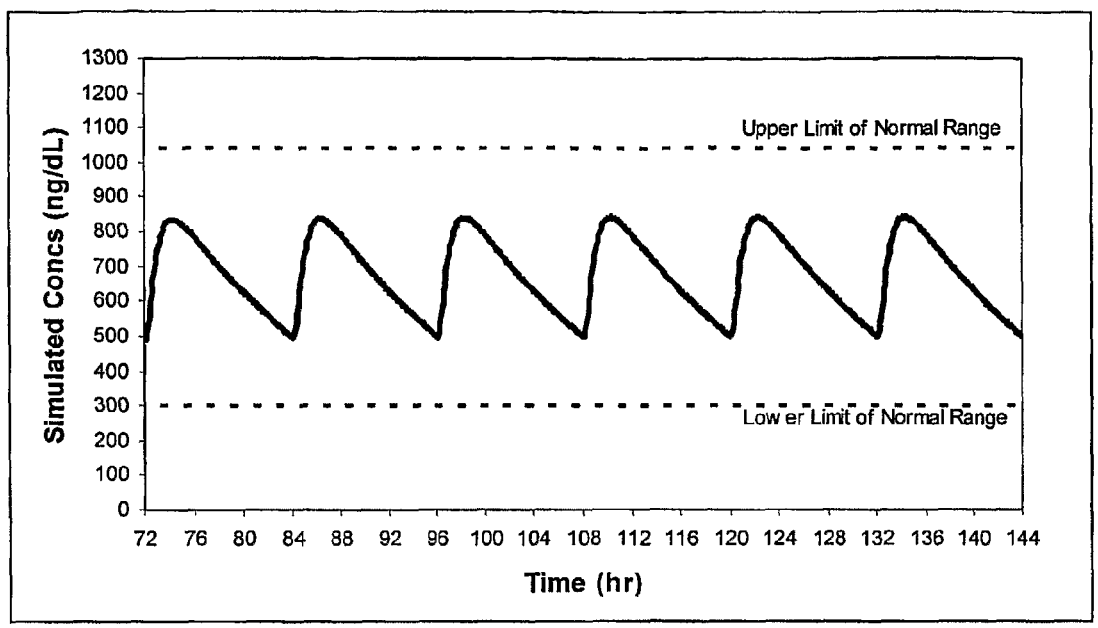
FIG. 7 depicts a steady-state pharmacokinetic profile of the serum concentration of testosterone upon ingestion of a formulation of TP, which provides and intermediate elimination half-life and a Tmax preferably compatible with maximal activity soon after walking while reducing the extent of fluctuation to the physiological level with twice-daily dosing.
Figure 8:
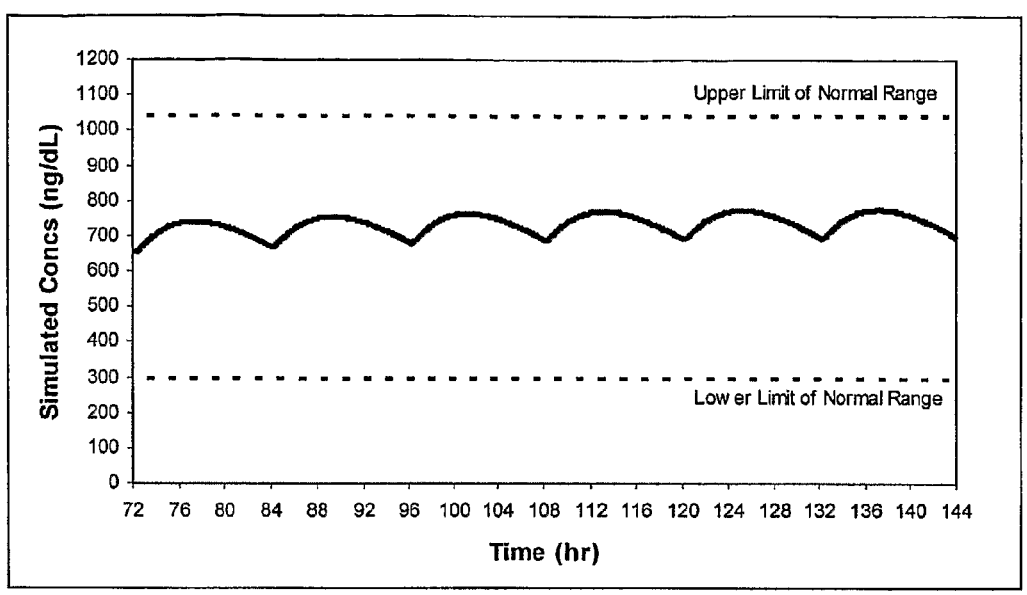
FIG. 8 depicts a steady-state pharmacokinetic profile of the serum concentration of testosterone upon ingestion of a formulation of TP, which provides a longer elimination half-life and a delayed Tmax, preferably compatible with maximal activity about awakening time following bedtime administration. This formulation reduces the extent of fluctuation to the physiological levels of testosterone with twice-daily dosing.

The present invention provides pharmaceutical delivery systems, preferably oral, for hydrophobic drugs. Accordingly, while the instant invention will be described, to some extent, with reference to oral delivery systems, the present invention may be suitable for topical and intramuscular injection. Further, hydrophobic drugs defined herein encompass both those drugs that are inherently hydrophobic (i.e., having a log P of at least 2) as well as otherwise hydrophilic medicaments that have been rendered hydrophobic with suitable modification (e.g., conjugation to fatty acids and/or lipids). (Log P is the log of the octanol-water or buffer partition coefficient and can be determined by a variety of methods for those skilled in the art. The higher the value of log P, the greater the lipophilicity and thus lipid solubility of the chemical entity in question.)

In one embodiment of the present invention, testosterone and/or esters at the C-17 position of the testosterone molecule, alone or in combination with other active ingredients, may be orally delivered using the inventive delivery system. While many of the embodiments of the present invention will be described and exemplified with the palmitic acid ester of testosterone (also referred to as "testosterone palmitate" or "TP"), the scope of the present invention should not be construed nor limited solely to the delivery of TP or testosterone per se. In fact, it should be readily apparent to one of ordinary skill in the art from the teachings herein that the inventive drug delivery systems and compositions therefrom may be suitable for oral delivery of other testosterone esters, such as short-chain ($C_2$-$C_6$), medium-chain ($C_7$-$C_{13}$) and long-chain ($C_{14}$-$C_{24}$) fatty acid esters, preferably long-chain fatty acid esters of testosterones and numerous hydrophobic medicaments. Such suitable medicaments, which may be formulated in accordance with the present invention include, but should not be limited to, the following:

Analgesics and anti-inflammatory agents: aloxiprin, auranofin, azapropazone, benorylate, diflunisal, etodolac, fenbufen, fenoprofen calcim, flurbiprofen, ibuprofen, indomethacin, ketoprofen, meclofenamic acid, mefenamic acid, nabumetone, naproxen, oxyphenbutazone, phenylbutazone, piroxicam, sulindac.

Anthelmintics: albendazole, bephenium hydroxynaphthoate, cambendazole, dichlorophen, ivermectin, mebendazole, nitazoxamide, oxamniquine, oxfendazole, oxantel embonate, praziquantel, pyrantel embonate, thiabendazole.

Anti-arrhythmic agents: amiodarone HCl, disopyramide, flecainide acetate, quinidine sulphate.

Anti-bacterial agents: benethamine penicillin, cinoxacin, ciprofloxacin HCl, clarithromycin, clofazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphamerazine, sulphacetamide, sulphadiazine, sulphafurazole, sulphamethoxazole, sulphapyridine, tetracycline, trimethoprim.

Anti-coagulants: dicoumarol, dipyridamole, nicoumalone, phenindione.

Anti-depressants: amoxapine, maprotiline HCl, mianserin HCl, nortriptyline HCl, trazodone HCl, trimipramine maleate.

Anti-diabetics: acetohexamide, chlorpropamide, glibenclamide, gliclazide, glipizide, tolazamide, tolbutamide.

Anti-epileptics: beclamide, carbamazepine, clonazepam, ethotoin, methoin, methsuximide, methylphenobarbitone, oxcarbazepine, paramethadione, phenacemide, phenobarbitone, phenyloin, phensuximide, primidone, sulthiame, valproic acid.

Anti-fungal agents: amphotericin, butoconazole nitrate, clotrimazole, econazole nitrate, fluconazole, flucytosine, griseofulvin, itraconazole, ketoconazole, miconazole, natamycin, nystatin, sulconazole nitrate, terbinafine HCl, terconazole, tioconazole, undecenoic acid.

Anti-gout agents: allopurinol, probenecid, sulphin-pyrazone.

Anti-hypertensive agents: amlodipine, benidipine, darodipine, dilitazem HCl, diazoxide, felodipine, guanabenz acetate, isradipine, minoxidil, nicardipine HCl, nifedipine, nimodipine, phenoxybenzamine HCl, prazosin HCl, reserpine, terazosin HCl.

Anti-malarials: amodiaquine, chloroquine, chlorproguanil HCl, halofantrine HCl, mefloquine HCl, proguanil HCl, pyrimethamine, quinine sulphate.

Anti-migraine agents: dihydroergotamine mesylate, ergotamine tartrate, methysergide maleate, pizotifen maleate, sumatriptan succinate.

Anti-muscarinic agents: atropine, benzhexol HCl, biperiden, ethopropazine HCl, hyoscyamine, mepenzolate bromide, oxyphencylcimine HCl, tropicamide.

Anti-neoplastic agents and Immunosuppressants: aminoglutethimide, amsacrine, azathioprine, busulphan, chlorambucil, cyclosporin, dacarbazine, estramustine, etoposide, lomustine, melphalan, mercaptopurine, methotrexate, mitomycin, mitotane, mitozantrone, procarbazine HCl, tamoxifen citrate, testolactone.

Anti-protazoal agents: benznidazole, clioquinol, decoquinate, diiodohydroxyquinoline, diloxanide furoate, dinitolmide, furzolidone, metronidazole, nimorazole, nitrofurazone, omidazole, timidazole.

Anti-thyroid agents: carbimazole, propylthiouracil.

Anxiolytic, sedatives, hypnotics and neuroleptics: alprazolam, amylobarbitone, barbitone, bentazepam, bromazepam, bromperidol, brotizolam, butobarbitone, carbromal, chlordiazepoxide, chlormethiazole, chlorpromazine, clobazam, clotiazepam, clozapine, diazepam, droperidol, ethinamate, flunanisone, flunitrazepam, fluopromazine, flupenthixol decanoate, fluphenazine decanoate, flurazepam, haloperidol, lorazepam, lormetazepam, medazepam, meprobamate, methaqualone, midazolam, nitrazepam, oxazepam, pentobarbitone, perphenazine pimozide, prochlorperazine, sulpiride, temazepam, thioridazine, triazolam, zopiclone.

Beta-blockers: acebutolol, alprenolol, atenolol, labetalol, metoprolol, nadolol, oxprenolol, pindolol, propranolol.

Cardiac Inotropic agents: amrinone, digitoxin, digoxin, enoximone, lanatoside C, medigoxin.

Corticosteroids: beclomethasone, betamethasone, budesonide, cortisone acetate, desoxymethasone, dexamethasone, fludrocortisone acetate, flunisolide, flucortolone, fluticasone propionate, hydrocortisone, methylprednisolone, prednisolone, prednisone, triamcinolone.

Diuretics: acetazolamide, amiloride, bendrofluazide, bumetanide, chlorothiazide, chlorthalidone, ethacrynic acid, frusemide, metolazone, spironolactone, triamterene.

Anti-parkinsonian agents: bromocriptine mesylate, lysuride maleate.

Gastro-intestinal agents: bisacodyl, cimetidine, cisapride, diphenoxylate HCl, domperidone, famotidine, loperamide, mesalazine, nizatidine, omeprazole, ondansetron HCl, ranitidine HCl, sulphasalazine.

Histamine $H_1$-Receptor Antagonists: acrivastine, astemizole, cinnarizine, cyclizine, cyproheptadine HCl, dimenhydrinate, flunarizine HCl, loratadine, meclozine HCl, oxatomide, terrenadine.

Lipid regulating agents: bezafibrate, clofibrate, fenofibrate, gemfibrozil, probucol.

Nitrates and other anti-anginal agents: amyl nitrate, glyceryl trinitrate, isosorbide dinitrate, isosorbide mononitrate, pentaerythritol tetranitrate.

Nutritional agents: betacarotene, vitamin A, vitamin $B_2$, vitamin D, vitamin E, vitamin K.

Opioid analgesics: codeine, dextropropyoxyphene, diamorphine, dihydrocodeine, meptazinol, methadone, morphine, nalbuphine, pentazocine.

Sex hormones: clomiphene citrate, danazol, ethinyloestradiol, medroxyprogesterone acetate, mestranol, methyltestosterone, norethisterone, norgestrel, oestradiol, conjugated oestrogens, progesterone, synthetic progestins (also referred to as progestogens), stanozolol, stiboestrol, tibolone, testosterone, esters of testosterone, including esters of oleic acid, linoleic acid, linolenic acid, stearic acid, myristic acid, lauric acid, palmitic acid, capric or decanoic acid octanoic or caprylic acid, pelargonic acid, undecanoic acid, tridecanoic acid, pentadecanoic acid, and the branched chain, cyclic analogues of these acids, testosterone analogues such as methyl-nortestosterone, and combinations thereof. Synthetic progestins include, for example, levonorgestrel, levonorgestrel butanoate, drospirenone, norethisterone, desogestrel, etonorgestrel and medroxyprogesterone.

Gonadotropin releasing hormone (GnRH) antagonists that are orally active.

Stimulants: amphetamine, dexamphetamine, dexfenfluramine, fenfluramine, mazindol.

Mixtures of hydrophobic drugs may, of course, be used where therapeutically effective. For example, the combination of testosterone palmitate with an orally active inhibitor or Type I or Type II 5α-reductase or the combination of testosterone palmitate with a synthetic progestin may be preferable in some embodiments.

Drug delivery systems of the present invention and compositions comprising same, comprise a hydrophobic drug or drugs dissolved in a lipophilic surfactant and a hydrophilic surfactant. A lipophilic surfactant as defined herein has a hydrophilic-lipophilic balance (HLB) less than 10, and preferably less than 5. A hydrophilic surfactant as defined herein has an HLB of greater than 10. (HLB is an empirical expression for the relationship of the hydrophilic and hydrophobic groups of a surface active amphiphilic molecule, such as a surfactant. It is used to index surfactants and its value varies from about 1 to about 45. The higher the HLB, the more water soluble the surfactant.)

According to one aspect of the present invention, each of the components of the delivery system (i.e., the lipophilic and hydrophilic surfactants) individually have solvent characteristics and contribute, in part, to solubilizing the active ingredient. Those lipophilic surfactants that contribute substantially to dissolving the drug are defined herein as a "primary" solvent. Primary solvents can also provide "sustained-release" or "controlled-release" characteristics to the drug delivery system. "Secondary" solvents are hydrophilic surfactants that also solubilize the drug, albeit to a lesser extent than a primary solvent. In addition to dissolving the drug, secondary solvents facilitate the dispersion of the delivery system in aqueous media or intestinal fluids and subsequent release of the drug. In cases where the secondary solvent is a high melting point hydrophilic surfactant, it can also provide for a sustained drug release, acting synergistically with the lipophilic surfactant.

A hydrophilic surfactant component may be necessary to achieve desirable emission of the drug from within the formulation. That is, a hydrophilic surfactant may be required to free the drug from within the lipid carrier matrix, or primary solvent. In this respect, a high HLB surfactant, such as Cremophor RH40, can generally suffice. In some formulations incorporating high levels of solubilized TP, the inventors have observed that in the absence of a high HLB surfactant, there can be substantially no release of the drug from blends solely comprising lipophilic surfactants. The levels of the high HLB surfactant can be adjusted to provide optimum drug release without compromising the solubilization of the active ingredient.

The lipophilic surfactant component, in some embodiments, may further comprise a "controlled-release" surfactant. In other words, in addition to being a solvent for the drug, the lipophilic surfactant may also provide a semi-solid and sustained release (SR) matrix. Many semi-solid/SR excipients are available to one of ordinary skill in the art, but those that additionally are good solvents for the drug are desirable in the instant invention. Thus, preference should be given to semi-solid lipid excipients having high solubilization potential for the drug. In one aspect, "controlled-release" lipophilic surfactants exhibit a melting point of about 25° C. to about 80° C., preferably about 35° C. to about 65° C., and more preferably 40° C. to about 60° C.

To be sure, however, "controlled-release" surfactants need not be limited to lipophilic surfactants alone. Indeed, some hydrophilic surfactants in compositions of the instant invention may also provide controlled-release characteristics in conjunction with a lipophilic surfactant.

Lipophilic surfactants suitable in drug delivery systems of the present invention include:

Fatty acids ($C_6$-$C_{24}$, preferably $C_{10}$-$C_{24}$, more preferably $C_{14}$-$C_{24}$), for example, octanoic acid, decanoic acid, undecanoic acid, lauric acid, myristic acid, palmitic acid, stearic acid, oleic acid, linoleic acid, and linolenic acid. Stearic acid and palmitic acid are preferred.

Mono- and/or di-glycerides of fatty acids, such as Imwitor 988 (glyceryl mono-/di-caprylate), Imwitor 742 (glyceryl mono-di-caprylate/caprate), Imwitor 308 (glyceryl mono-caprylate), Imwitor 191 (glyceryl mono-stearate), Softigen 701 (glyceryl mono-/di-ricinoleate), Capmul MCM (glyceryl caprylate/caprate), Capmul MCM(L) (liquid form of Capmul MCM), Capmul GMO (glyceryl mono-oleate), Capmul GDL (glyceryl dilaurate), Maisine (glyceryl mono-linoleate), Peceol (glyceryl mono-oleate), Myverol 18-92 (distilled monoglycerides from sunflower oil) and Myverol 18-06 (distilled monoglycerides from hydrogenated soybean oil), Precirol ATO 5 (glyceryl palmitostearate) and Gelucire 39/01 (semi-synthetic glycerides, i.e., $C_{12\text{-}18}$ mono-, di- and tri-glycerides). The preferred members of this class of lipophilic surfactants are the partial glycerides of oleic, palmitic and stearic acids and blends thereof.

Acetic, succinic, lactic, citric and/or tartaric esters of mono- and/or di-glycerides of fatty acids, for example, Myvacet 9-45 (distilled acetylated monoglycerides), Miglyol 829 (caprylic/capric diglyceryl succinate), Myverol SMG (mono/di-succinylated monoglycerides), Imwitor 370 (glyceryl stearate citrate), Imwitor 375 (glyceryl monostearate/citrate/lactate) and Crodatem T22 (diacetyl tartaric esters of monoglycerides).

Propylene glycol mono- and/or di-esters of fatty acids, for example, Lauroglycol (propylene glycol monolaurate), Mirpyl (propylene glycol monomyristate), Captex 200 (propylene glycol dicaprylate/dicaprate), Miglyol 840 (propylene glycol dicaprylate/dicaprate) and Neobee M-20 (propylene glycol dicaprylate/dicaprate).

Polyglycerol esters of fatty acids such as Plurol oleique (polyglyceryl oleate), Caprol ET (polyglyceryl mixed fatty acids) and Drewpol 10.10.10 (polyglyceryl oleate).

Castor oil ethoxylates of low ethoxylate content (HLB<10) such as Etocas 5 (5 moles of ethylene oxide reacted with 1 mole of castor oil) and Sandoxylate 5 (5 moles of ethylene oxide reacted with 1 mole of castor oil).

Acid and ester ethoxylates formed by reacting ethylene oxide with fatty acids or glycerol esters of fatty acids (HLB<10) such as Crodet 04 (polyoxyethylene (4) lauric acid), Cithrol 2MS (polyoxyethylene (2) stearic acid), Marlosol 183 (polyoxyethylene (3) stearic acid) and Marlowet G12DO (glyceryl 12 EO dioleate). Sorbitan esters of fatty acids, for example, Span 20 (sorbitan monolaurate), Crill 1 (sorbitan monolaurate) and Crill 4 (sorbitan mono-oleate).

Transesterification products of natural or hydrogenated vegetable oil triglyceride and a polyalkylene polyol (HLB<10), e.g. Labrafil M1944CS (polyoxyethylated apricot kernel oil), Labrafil M2125CS (polyoxyethylated corn oil) and Gelucire 37/06 (polyoxyethylated hydrogenated coconut). Labrafil M1944CS is preferred.

Alcohol ethyoxylates (HLB<10), e.g. Volpo N3 (polyoxyethylated (3) oleyl ether), Brij 93 (polyoxyethylated (2) oleyl ether), Marlowet LA4 (polyoxyethylated (4) lauryl ether) and Pluronics, for example, Polyoxyethylene-polyoxypropylene co-polymers and block co-polymers (HLB<10) e.g. Synperonic PE L42 (HLB=8) and Synperonic PE L61 (HLB=3)

Mixtures of suitable lipophilic surfactants, such as those listed above, may be used if desired, and in some instances are found to be advantageous. For instance, glycerol palmitate and glycerol stearate esters alone and in blends are preferred lipophilic surfactants and controlled-release matrices.

Of the lipophilic surfactants listed above, those suitable as a "controlled-release" component include, but are not limited to, stearic acid, palmitic acid, and their glycerol and PEG esters, Precirol AT05, Imwitor 191, Myverol 18-06, Imwitor 370, Imwitor 375, Caprol ET, Cithrol 2MS, Marosol 183, Gelucire 39/01 and combinations thereof.

Any pharmaceutically acceptable hydrophilic surfactant (i.e., having an HLB value greater than 10) may be used in the present invention. Some non-limiting examples include:

Polyoxyethylene sorbitan fatty acid derivates e.g. Tween 20 (polyoxyethylene (20) monolaureate), Tween 80 (polyoxyethylene (20) monooleate), Crillet 4 (polyoxyethylene (20) monooleate) and Montanox 40 (polyoxyethylene (20) monopalmitate). Tween 80 (Polysorbate 80) is preferred.

Castor oil or hydrogenated caster oil ethoxylates (HLB>10), e.g. Cremophor EL (polyoxyethylene (35) castor oil), Cremophor RH40 (polyoxyethylene (40) hydrogenated castor oil), Etocas 40 (polyoxyethylene (40) castor oil), Nikkol HCO-60 (polyoxyethylene (60) hydrogenated castor oil), Solutol HS-15 (polyethylene glycol 660 hydroxystearate), Labrasol (caprylocaproyl macrogol-8 glycerides), α-tocopherol-polyethylene glycol-1000-succinate (TPGS) and ascorbyl-6 palmitate. Cremophor RH40 is preferred.

Gelucires, preferably Gelucire 50/13 (PEG mono- and diesters of palmitic and stearic acids. (In reference to Gelucires, the first number (i.e., 50) corresponds to the melting point of the material and the second (i.e., 13) to the HLB number.)

Fatty acid ethoxylates (HLB>10), e.g. Myrj 45 (polyoxyethylene (8) stearate), Tagat L (polyoxyethylene (30) monolaurate), Marlosol 1820 (polyoxyethylene (20) stearate) and Marlosol OL15 (polyoxyethylene (15) oleate). Myrj 45 is preferred.

Alcohol ethoxylates (HLB>10), e.g. Brij 96 (polyoxyethylene (10) oleyl ether), Volpo 015 (polyoxyethylene (15) oleyl ether), Marlowet OA30 (polyoxyethylene (30) oleyl ether) and Marlowet LMA20 (polyoxyethylene (20) $C_{12}$-$C_{14}$ fatty ether).

Polyoxyethylene-polyoxypropylene co-polymers and block co-polymers (HLB>10), that are commercially available under the trade name Pluronics or Poloxamers, such as Poloxamers 188 and 407 also known as Syperonic PE L44 (HLB=16) and Syperonic F127 (HLB=22), respectively.

Anionic surfactants e.g. sodium lauryl sulphate, sodium oleate and sodium dioctylsulphosuccinate.

Alkylphenol surfactants (HLB>10) e.g. Triton N-101 (polyoxyethylene (9-10) nonylphenol) and Synperonic NP9 (polyoxyethylene (9) nonylphenol).

Of the hydrophilic surfactants listed above, those suitable as a "controlled-release" surfactant include, but are not limited to Gelucires of high HLB value, such as Gelucire 50/13.

As mentioned, in one aspect of the present invention, each of the components of the delivery system (i.e., the lipophilic and hydrophilic surfactants) individually has solvent characteristics and contributes, in part, to solubilizing the active ingredient. In this way, without being bound by or limited to theory, the present invention does not require additional solvents, such as additional digestible oils and/or cosolvents, but these may be optionally included in the inventive systems and formulations.

A digestible oil is defined herein as an oil that is capable of undergoing de-esterification or hydrolysis in the presence of pancreatic lipase in vivo under normal physiological conditions. Specifically, digestible oils may be complete glycerol triesters of medium chain ($C_7$-$C_{13}$) or long chain ($C_{14}$-$C_{22}$) fatty acids with low molecular weight (up to $C_6$) mono-, di- or polyhydric alcohols. Some examples of digestible oils for use in this invention thus include: vegetable oils (e.g., soybean oil, safflower seed oil, corn oil, olive oil, castor oil, cottonseed oil, arachis oil, sunflower seed oil, coconut oil, palm oil, rapeseed oil, evening primrose oil, grape seed oil, wheat germ oil, sesame oil, avocado oil, almond, borage, peppermint and apricot kernel oils) and animal oils (e.g., fish liver oil, shark oil and mink oil).

As well, optional cosolvents suitable with the instant invention are, for example, water, short chain mono-, di-, and polyhydric alcohols, such as ethanol, benzyl alcohol, glycerol, propylene glycol, propylene carbonate, polyethylene glycol with an average molecular weight of about 200 to about 10,000, diethylene glycol monoethyl ether (e.g., Transcutol HP), and combinations thereof.

Other optional ingredients which may be included in the compositions of the present invention are those which are conventionally used in the oil-based drug delivery systems, e.g. antioxidants such as tocopherol, tocopherol acetate, ascorbic acid, butylhydroxytoluene, butylhydroxyanisole and propyl gallate; pH stabilizers such as citric acid, tartaric acid, fumaric acid, acetic acid, glycine, arginine, lysine and potassium hydrogen phosphate; thickeners/suspending agents such as hydrogenated vegetable oils, beeswax, colloidal silicon dioxide, mannitol, gums, celluloses, silicates, bentonite; flavoring agents such as cherry, lemon and aniseed flavors; sweeteners such as aspartame, acesulfane K, sucralose, saccharin and cyclamates; etc.

The relative proportions of the lipophilic surfactant and hydrophilic surfactant in the preferred hydrophobic drug carrier system of this invention are, in general, not especially critical, save that the concentration of lipophilic and hydrophilic surfactants must be sufficient to solubilize the hydrophobic drug, yet release same both in vitro and in vivo. It should be noted that in some embodiments of the invention, one hydrophobic drug may serve as a lipid vehicle for another. More specifically, for example, a testosterone ester may serve as a carrier for testosterone. Even more specifically, TP may serve as a lipid vehicle for testosterone. As well, TP may serve, in some embodiments, as its own "controlled-release" vehicle, which may obviate the need for additional "controlled-release" lipids mentioned above.

Generally, the following relative concentrations, by weight, are preferred (the percentages are based on the total content of hydrophilic surfactant and lipophilic surfactant(s)):
Hydrophilic surfactant: 5-60%, more preferably 15-45%, and most preferably 30-40%
Lipophilic surfactant: 10-90%, more preferably 20-80%, and most preferably 30-60%
Lipophilic "controlled-release" surfactant: 1-40%, more preferably 2.5-30%, and most preferably 5-25%.

The concentration of drug in the final pharmaceutical formulation will be that which is required to provide the desired therapeutic effect from the drug concerned, but generally will lie in the range 0.1% to 50% by weight, preferably between about 10% to 30% by weight, and most preferably about 10% and 20% by weight, based on the weight of the final composition. However, in many instances, because the present compositions may have better bioavailability than known compositions of the drug concerned, the drug concentration may be reduced as compared with the conventional preparations without loss of therapeutic effect. With specific reference to testosterone therapy, the present inventors have learned that the use of the palmitate ester of T, in particular, is desirable. Indeed, once absorbed, the long and fully saturated chain of the fatty acid on T slows the rate of hydrolysis of the ester bond thus prolonging the circulation of the TP and consequently T. For example, formulations of the present invention (e.g., formulation nos. 50 and 54 (below)) comprising TP have a T half-life of about 8-9 hours. By comparison, the half-life for T is about 30 minutes and that of T-undecanoate is about 1.5 hours.

In other embodiments, formulations of the present invention may have self-emulsifying properties, forming a fine emulsion upon dilution with aqueous media or intestinal fluids in vivo. In other words, the formulations may have high surfactant and lipid content designed for adequate dispersion upon mixing with an aqueous medium. Qualitative description of the self-emulsification property of the inventive formulations can be visually observed during the dissolution of same in vitro. On the other hand, quantitative measurements may be taken of the particle size of the emulsified droplets using laser light scattering and/or turbidity measurements in the dissolution medium by UV/VIS spectrophotometer. Any of these methodologies are available and known to one of ordinary skill in the art.

The pharmaceutical compositions according to the present invention may be liquid, semi-solid, or solid at ambient temperatures, but preferably are presented as liquids or semi-solids. Solid preparations are defined as solid, powdered medicaments blended with powdered excipients and directly filled into hard gelatin or cellulose capsule or compressed into a tablet. The instant invention, however, preferably comprises a solid, powdered medicament (e.g., TP) that is solubilized in the presence of the lipid surfactant excipients (e.g., any combination of the lipophilic and hydrophilic surfactants noted above). Accordingly, the melting point of the surfactants used is one factor that can determine whether the resulting composition will be liquid or semi-solid at ambient temperature. Particularly preferred compositions of the present invention are liquid or semi-solid oral unit dosage forms, more preferably filled into hard or soft capsules, e.g. gelatin or cellulose capsules. The technology for encapsulating lipid-based pharmaceutical preparations is well known to one of ordinary skill in the art. As the inventive delivery systems and formulations described herein are not limited to any one encapsulation method, specific encapsulation techniques will not be further discussed.

The drug carrier systems and pharmaceutical preparations according to the present invention may be prepared by conventional techniques for lipid-based drug carrier systems. In a typical procedure for the preparation of the preferred carrier systems of this invention, the lipophilic surfactant is weighed out into a suitable stainless steel vessel and the hydrophilic surfactant is then weighed and added to the container. Mixing of the two components may be effected by use of a homogenizing mixer or other high shear device. If the material is solid at room temperature, sufficient heat is applied to ensure melting and fluidity without chemical decomposition.

The lipophilic "controlled-release" surfactant is then added, if desired, to the two other components in the stainless steel vessel and mixed using the appropriate equipment. The hydrophobic drug is then weighed and added to the combined lipid mixture and mixing continued until either a homogenous solution is prepared. The formulation may be de-aerated before encapsulation in either soft or hard capsules. In some instances the fill formulation may be held at elevated temperature using a suitable jacketed vessel to aid processing.

Returning now to the delivery of testosterone, in one embodiment of the present invention, drug delivery systems of the present invention may be suitable for testosterone therapy. Testosterone is the main endogenous androgen in men. Leydig cells in the testes produce approximately 7 mg of testosterone each day resulting in serum concentrations ranging from about 300 to about 1100 ng/dL. Women also synthesize testosterone in both the ovary and adrenal gland, but the amount is about one-tenth that observed in eugonadal men. The majority (about 98%) of circulating testosterone is bound to sex hormone binding globulin and is biologically active only when released to the free form. The term "free" is thus defined as not being bound to or confined within, for example, biomolecules, cells and/or lipid matrices of the inventive formulations described herein. Generally, "free" medicaments described herein refer to medicament that is accessible to metabolic enzymes circulating in serum.

While the present invention should not be limited to the delivery of testosterone or any particular ester thereof, TP has been found to offer unique chemical and physical characteristics that make its use preferable in some embodiments. The present inventors have learned that the palmitic acid ester of testosterone, in particular, can yield superior bioavailability to that found with other equivalent esters (e.g., testosterone undecanoate (TU)). Without being held to or bound by theory, it is believed that TP is superior, in part, to other testosterone esters, because it has a particularly high log P compared to similar analogs. (The log P for TP is greater than 9 compared to a log P for TU of about 6.5)

Consequently, TP absorbed into the bloodstream may passively diffuse into red blood cells (RBCs) circulating in the blood. Specifically, because palmitic acid is both a significant component of the RBC membrane and has been shown to be transported across this membrane, TP is better suited to be in an equilibrium with and pass said membrane. In this manner, some portion of the total concentration of free TP at any given time may be found within RBCs. Further, when confined to a RBC, any TP therein is shielded from the esterases found in the serum. As the conversion of TP to testosterone is a direct consequence of esterase activity, greater inaccessibility to the esterases is expected to prolong the half-life of TP. For this reason, it is believed that the residence time of TP in the blood is greater than that would be expected from other saturated esters of shorter hydrocarbon chain-length.

What is more, the use of TP, in contrast to that for other orally administered testosterone esters, does not appear to dramatically elevate serum dihydrotestosterone ("DHT")

above physiological levels, which are typically about 1/10th that of testosterone (i.e., about 30 to 100 ng/dL) in eugonadal men. Testosterone interacts with respective androgen receptors either directly or following its conversion to DHT via the action of 5α-reductase. DHT is a more potent androgen than testosterone and its elevated levels are thought by some scientists to increase the risk of prostate cancer. Elevated levels of DHT are a noted problem with the administration of, for example, TU. In this way, TP provides yet another unexpected advantage over other testosterone esters.

Specific embodiments of the instant invention will now be described in non-limiting examples. Table 1 provides composition details of various formulations of testosterone (T) or testosterone-esters (T-esters), in accordance with the teachings of the instant invention. For calculation purposes, 1 mg of T is equivalent to: 1.39 mg T-enanthate; 1.58 mg T-undecanoate; 1.43 mg T-cypionate, and 1.83 mg T-palmitate. TP is a preferred T-ester in some of the formulations listed below. The compositions details of Table 1 (mg/capsule and wt. percentage) are based on 800 mg fill weight per '00' hard gelatin capsule. However, at testosterone-ester amounts less than about 100 mg/capsule, the formulations may be proportionally adjusted for smaller total fill weights that would permit use of smaller hard gelatin capsules (e.g., '0' size).

As well, it should be apparent to one of ordinary skill in the art that many, if not all, of the surfactants within a category (e.g., lipophilic, hydrophilic, etc.) may be exchanged with another surfactant from the same category. Thus, while Table 1 lists formulations comprising Labrafil M1944CS (HLB=3) and Precirol ATO5 (HLB=2), one of ordinary skill in the art should recognize other lipophilic surfactants (e.g., those listed above) may be suitable as well. Similarly, while Table 1 lists formulations comprising Cremophor RH40 (HLB=13) and Labrasol (HLB=14), one of ordinary skill in the art should recognize other hydrophilic surfactants (e.g., those listed above) may be suitable.

TABLE 1

| ID | T or T-ester | Labrafil M1944CS | Precirol ATO5 | Cremophor RH40 | Labrasol |
|---|---|---|---|---|---|
| A | 400 | 109.68 | 66.49 | 223.83 | — |
|   | 50.00% | 13.71% | 8.31% | 27.98% | — |
| B | 360 | 120.64 | 73.14 | 246.21 | — |
|   | 45.00% | 15.08% | 9.14% | 30.78% | — |
| C | 320 | 131.61 | 79.79 | 268.60 | — |
|   | 40.00% | 16.45% | 9.97% | 33.57% | — |
| D | 280 | 142.58 | 86.44 | 290.98 | — |
|   | 35.00% | 17.82% | 10.80% | 36.37% | — |
| E | 240 | 153.55 | 93.09 | 313.36 | — |
|   | 30.00% | 19.19% | 11.64% | 39.17% | — |
| F | 228.32 | 156.75 | 95.03 | 319.9 | — |
|   | 28.54% | 19.59% | 11.88% | 39.99% | — |
| G | 200 | 164.52 | 99.74 | 335.75 | — |
|   | 25.00% | 20.56% | 12.47% | 41.97% | — |
| H | 160 | 175.48 | 106.39 | 358.13 | — |
|   | 20.00% | 21.94% | 13.30% | 44.77% | — |
| I | 120 | 186.45 | 113.04 | 380.51 | — |
|   | 15.00% | 23.31% | 14.13% | 47.56% | — |
| J | 80 | 197.42 | 119.69 | 402.90 | — |
|   | 10.00% | 24.68% | 14.96% | 50.36% | — |
| K | 40 | 208.39 | 126.33 | 425.28 | — |
|   | 5.00% | 26.05% | 15.79% | 53.16% | — |
| L | 20 | 213.87 | 129.66 | 436.47 | — |
|   | 2.50% | 26.73% | 16.21% | 54.56% | — |
| M | 400 | 199.97 | 66.62 | 133.40 | — |
|   | 50.00% | 25.00% | 8.33% | 16.68% | — |
| N | 360 | 219.97 | 73.29 | 146.74 | — |
|   | 45.00% | 27.50% | 9.16% | 18.34% | — |
| O | 320 | 239.97 | 79.95 | 160.08 | — |
|   | 40.00% | 30.00% | 9.99% | 20.01% | — |

TABLE 1-continued

| ID | T or T-ester | Labrafil M1944CS | Precirol ATO5 | Cremophor RH40 | Labrasol |
|---|---|---|---|---|---|
| P | 280 | 259.96 | 86.61 | 173.42 | — |
|   | 35.00% | 32.50% | 10.83% | 21.68% | — |
| Q | 240 | 279.96 | 93.27 | 186.76 | — |
|   | 30.00% | 35.00% | 11.66% | 23.35% | — |
| R | 228.32 | 285.8 | 95.22 | 190.66 | — |
|   | 28.54% | 35.73% | 11.90% | 23.83% | — |
| S | 200 | 299.96 | 99.94 | 200.10 | — |
|   | 25.00% | 37.49% | 12.49% | 25.01% | — |
| T | 160 | 319.96 | 106.60 | 213.45 | — |
|   | 20.00% | 39.99% | 13.32% | 26.68% | — |
| U | 120 | 339.95 | 113.26 | 226.79 | — |
|   | 15.00% | 42.49% | 14.16% | 28.35% | — |
| V | 80 | 359.95 | 119.92 | 240.13 | — |
|   | 10.00% | 44.99% | 14.99% | 30.02% | — |
| W | 40 | 379.95 | 126.59 | 253.47 | — |
|   | 5.00% | 47.49% | 15.82% | 31.68% | — |
| X | 20 | 389.95 | 129.92 | 260.14 | — |
|   | 2.50% | 48.74% | 16.24% | 32.52% | — |
| AA | 400 | 109.79 | 66.55 | 149.72 | 73.94 |
|   | 50.00% | 13.72% | 8.32% | 18.72% | 9.24% |
| BB | 360 | 120.77 | 73.21 | 164.69 | 81.33 |
|   | 45.00% | 15.10% | 9.15% | 20.59% | 10.17% |
| CC | 320 | 131.75 | 79.87 | 179.66 | 88.72 |
|   | 40.00% | 16.47% | 9.98% | 22.46% | 11.09% |
| DD | 280 | 142.73 | 86.52 | 194.64 | 96.12 |
|   | 35.00% | 17.84% | 10.82% | 24.33% | 12.01% |
| EE | 240 | 153.70 | 93.18 | 209.61 | 103.51 |
|   | 30.00% | 19.21% | 11.65% | 26.20% | 12.94% |
| FF | 228.32 | 156.91 | 95.12 | 213.98 | 105.67 |
|   | 28.54% | 19.61% | 11.89% | 26.75% | 13.21% |
| GG | 200 | 164.68 | 99.83 | 224.58 | 110.90 |
|   | 25.00% | 20.59% | 12.48% | 28.07% | 13.86% |
| HH | 160 | 175.66 | 106.49 | 239.55 | 118.30 |
|   | 20.00% | 21.96% | 13.31% | 29.94% | 14.79% |
| II | 120 | 186.64 | 113.14 | 254.52 | 125.69 |
|   | 15.00% | 23.33% | 14.14% | 31.82% | 15.71% |
| JJ | 80 | 197.62 | 119.80 | 269.50 | 133.09 |
|   | 10.00% | 24.70% | 14.97% | 33.69% | 16.64% |
| KK | 40 | 208.60 | 126.45 | 284.47 | 140.48 |
|   | 5.00% | 26.07% | 15.81% | 35.56% | 17.56% |
| LL | 20 | 214.09 | 129.78 | 291.95 | 144.18 |
|   | 2.50% | 26.76% | 16.22% | 36.49% | 18.02% |
| MM | 400 | 81.62 | 94.47 | 223.91 | — |
|   | 50.00% | 10.20% | 11.81% | 27.99% | — |
| NN | 360 | 89.78 | 103.92 | 246.30 | — |
|   | 45.00% | 11.22% | 12.99% | 30.79% | — |
| OO | 320 | 97.94 | 113.37 | 268.69 | — |
|   | 40.00% | 12.24% | 14.17% | 33.59% | — |
| PP | 280 | 106.10 | 122.81 | 291.08 | — |
|   | 35.00% | 13.26% | 15.35% | 36.39% | — |
| QQ | 240 | 114.27 | 132.26 | 313.47 | — |
|   | 30.00% | 14.28% | 16.53% | 39.18% | — |
| RR | 228.32 | 116.65 | 135.02 | 320.01 | — |
|   | 28.54% | 14.58% | 16.88% | 40.00% | — |
| SS | 200 | 122.43 | 141.71 | 335.86 | — |
|   | 25.00% | 15.30% | 17.71% | 41.98% | — |
| TT | 160 | 130.59 | 151.16 | 358.25 | — |
|   | 20.00% | 16.32% | 18.89% | 44.78% | — |
| UU | 120 | 138.75 | 160.60 | 380.64 | — |
|   | 15.00% | 17.34% | 20.08% | 47.58% | — |
| VV | 80 | 146.91 | 170.05 | 403.04 | — |
|   | 10.00% | 18.36% | 21.26% | 50.38% | — |
| WW | 40 | 155.08 | 179.50 | 425.43 | — |
|   | 5.00% | 19.38% | 22.44% | 53.18% | — |
| XX | 20 | 159.16 | 184.22 | 436.62 | — |
|   | 2.50% | 19.89% | 23.03% | 54.58% | — |

Figure 9:
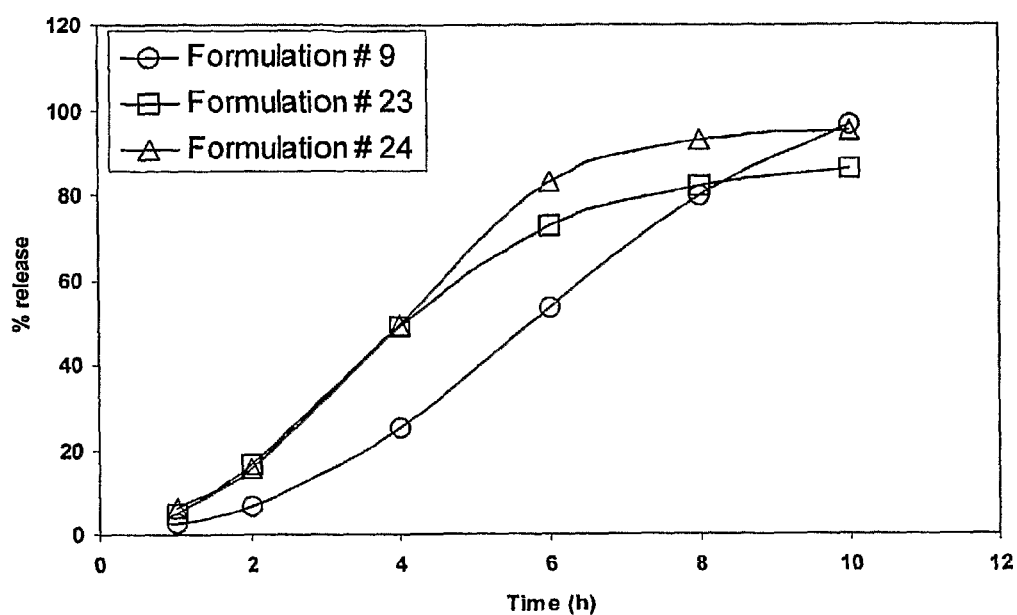
FIG. 9 shows dissolution curves of TP from three formulations (9, 23 and 24 the compositions of which are listed in Table 2) in a phosphate buffered dissolution medium incorporating TritonX-100 as a surfactant in accordance with the present invention.

Table 2 provides composition details of various TP formulations in accordance with the teachings of the instant invention and FIG. 9 provides in vitro dissolution of select formulations therein. TP may be synthesized through esterification of testosterone with palmitoyl chloride in an acetone/pyridine mixture. Testosterone palmitate crude is purified by filtration, crystallized from a methanol/methylene chloride mixture and washed with methanol. When necessary, recrystallization can be done from heptane, followed by washing with methanol.

TABLE 2

| F. No. | TP | LBR | PRC5 | OA | Peceol | TPGS | SO | CRH40 | L'sol | M'tol | Fill wt (mg)** |
|---|---|---|---|---|---|---|---|---|---|---|---|
| 1 | 228.32 (40.0) | 285.84 (50.0) | 57 (10.0) | | | | | | | | 570 |
| 2 | 228.32 (40.0) | | 57 (10.0) | 228 (40.0) | 57 (10.0) | | | | | | 570 |
| 3 | 228.32 (40.0) | 171 (30.0) | | 114 (20.0) | 57 (10.0) | | | | | | 570 |
| 4 | 228.32 (40.0) | 171 (30.0) | | 114 (20.0) | | 57 (10.0) | | | | | 570 |
| 5 | 228.32 (40.0) | | | 114 (20.0) | | 57 (10.0) | 171 (30.0) | | | | 570 |
| 6 | 228.32 (28.5) | 476 (59.5) | 95.2 (11.9) | | | | | | | | 800 |
| 7 | 228.32 (28.5) | | 95.2 (11.9) | 380.8 (47.6) | 95.2 (11.9) | | | | | | 800 |
| 8 | 228.32 (28.5) | | | 190.4 (23.8) | | 95.2 (11.9) | 285.6 (35.7) | | | | 800 |
| 9 | 228.32 (28.5) | 285.84 (35.7) | 95.2 (11.9) | | | | | 190.56 (23.8) | | | 800 |
| 10 | 228.32 (28.5) | | | 190.56 (23.8) | | 190.56 (23.8) | 190.56 (23.8) | | | | 800 |
| 11 | 228.32 (28.5) | 190.56 (23.8) | 95.2 (11.9) | 190.56 (23.8) | | | | 95.2 (11.9) | | | 800 |
| 12 | 228.32 (28.5) | 190.56 (23.8) | | 190.56 (23.8) | 95.2 (11.9) | | | | 95.2 (11.9) | | 800 |
| 13 | 228.32 (28.5) | 190.56 (23.8) | | | | | 190.56 (23.8) | 95.2 (11.9) | 95.2 (11.9) | | 800 |
| 14 | 228.32 (28.5) | | | 285 (35.7) | 95.2 (11.9) | 95.2 (11.9) | | | 95.2 (11.9) | | 800 |
| 15 | 228.32 (28.5) | 285.84 (35.7) | 20.0 (2.50) | | | | | 265.6 (33.2) | | | 800 |
| 16 | 228.32 (28.5) | 285.84 (35.7) | 20.0 (2.50) | 40.0 (5.00) | | | | 225.6 (28.2) | | | 800 |
| 17 | 228.32 (28.5) | 285.84 (35.7) | | 80.0 (10.0) | | | | 205.6 (25.7) | | | 800 |
| 18 | 228.32 (28.5) | 95.20 (11.9) | | 190.56 (23.8) | | | | 285.6 (35.7) | | | 800 |
| 19 | 228.32 (50.73) | 133.08 (29.57) | | | | | | 88.672 (19.7) | | | 450 |
| 20 | 228.32 (28.5) | 285.84 (35.7) | | | | | | 200.28 (25.0) | 85.72 (10.7) | | 800 |
| 21 | 228.32 (28.5) | 285.84 (35.7) | 95.2 (11.9) | | | | | | | 190.67 (23.8) | 800 |
| 22 | 228.32 (28.5) | 240.33 (30.0) | 65.7 (8.2) | | | | | 160.22 (20.0) | | 105.74 (13.2) | 800 |
| 23 | 228.32 (28.5) | 157.02 (19.6) | 95.2 (11.9) | | | | | 320.45 (40.0) | | | 800 |
| 24 | 228.32 (28.5) | 157.02 (19.6) | 95.2 (11.9) | | | | | 214.4 (26.8) | 105.74 (13.2) | | 800 |
| 25 | 228.32 (28.5) | 157.02 (19.6) | 65.6 (8.2) | | | | | 349.6 (43.7) | | | 800 |
| 26 | 228.32 (28.5) | 157.02 (19.6) | 40.0 (5.0) | | | | | 375.2 (46.9) | | | 800 |
| 57 | 182.65 (22.83) | 229.35 (28.7) | 20.0 (2.5) | | | | | 368.0 (46.0) | | | 800 |
| 58 | 120.0 (15.0) | 520.0 (65.0) | 20.0 (2.5) | | | | | 140.0 (17.5) | | | 800 |

*TP: Testosterone palmitate; LBR: Labrafil M1944CS; PRC5: PrecirolATO5; OA: Refined Oleic acid; SO: Refined Soybean oil; TPGS: D-α-tocopheryl PEG1000 succinate; CRH 40: Cremophor RH40; L'sol: Labrasol; M'tol: Mannitol
**Filled into size "0" capsule (570 mg) or "00" capsule (800 mg)

A preferred formulation of TP in accordance with the present invention is:

| Component | mg/capsule | %, w/w |
|---|---|---|
| Testosterone palmitate | 228.32 | 28.5 |
| Cremophor ® RH40 | 320.45 | 40.0 |
| Labrafil ® M 1944 CS | 157.02 | 19.6 |
| Precirol ® ATO 5 | 95.20 | 11.9 |
| Total: | 800 | 100.0 |

In some embodiments, it may be desirable to reduce the absolute concentration of testosterone and/or an ester thereof in order to promote a relatively faster release of the testosterone and/or ester from within the lipid vehicle. That is, it has been found, surprisingly, that reducing the concentration of TP, may in some cases, confer quicker release kinetics. For example, for significant release of TP within about a two hour period, a concentration of TP of less than about 23 percent by weight. In some embodiment, a weight percentage of less than about 20 is preferred, more preferably a weight percentage of less than about 18, and most preferably a weight percentage of less than about 15. Without being bound by or limited to theory, it is believed that TP at levels greater than about 23 weight percent may, in fact, retard its own release. For example, formulations according to the instant invention comprising less than about 23 weight percent TP can release 50-70% of the drug at 1 hour and 80 to near 100% at 2 hours. On the other hand, formulations according to the instant invention comprising greater than about 23 weight percent TP release less than 5% of the drug at 1 hr and less than 70% at 6 hours.

Figure 10:
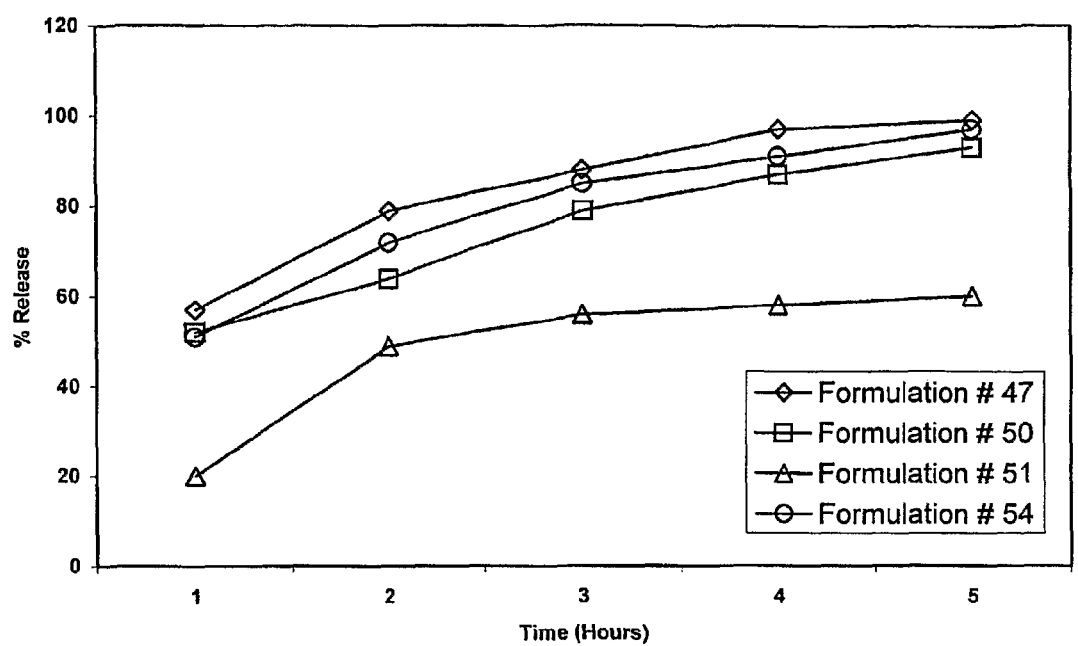
FIG. 10 shows dissolution curves of TP from three formulations (47, 50, 51 and 54 the compositions of which are listed in Table 3) in a phosphate buffered dissolution medium incorporating TritonX-100 as a surfactant in accordance with the present invention.

Table 3 provides composition details of various TP formulations, that in some cases, are at TP concentrations lower than those in Table 2 and in accordance with the teachings of the instant invention. FIG. 10 provides in vitro dissolution of select Table 3 formulations.

TABLE 3

| F. No. | TP | Labrasol | Cremophor RH40 | Oleic Acid | Capmul MCM(L) | Tween 80 | Precirol ATO5 | Gelucire 39/01 | Fill Wt. (mg) |
|---|---|---|---|---|---|---|---|---|---|
| 27 | 320.0 (40.0%) | — | 240.0 (30.0%) | 220.0 (27.5%) | — | — | 20.0 (2.5%) | — | 800 |
| 28 | 364.0 (45.5%) | — | 160.0 (20.0%) | 80 (10.0%) | 176.0 (22.0%) | — | 20.0 (2.5%) | — | 800 |
| 29 | 320.0 (40%) | 160.0 (20%) | — | — | 300.0 (37.5%) | — | — | 20.0 (2.5%) | 800 |
| 30, 34 | 120.0 (15.0%) | — | — | — | 680.0 (85.0%) | — | — | — | 800 |
| 31, 35 | 120.0 (15.0%) | — | — | — | 560.0 (70.0%) | 120.0 (15.0%) | — | — | 800 |
| 32 | 228.0 (28.5%) | — | 296.0 (37.0%) | 80 (10.0%) | 176.0 (22.0%) | — | 20.0 (2.5%) | — | 800 |
| 33 | 228.0 (28.5%) | 240.0 (30.0%) | — | — | 312.0 (39.0%) | — | — | 20.0 (2.5%) | 800 |
| 36 | 120.0 (15%) | — | 300.0 (37.5%) | 120.0 (15.0%) | 240.0 (30.0%) | — | 20.0 (2.5%) | — | 800 |
| 37 | 120.0 (15%) | 300.0 (37.5%) | — | — | 360.0 (45.0%) | — | — | 20.0 (2.5%) | 800 |
| 38 | 176.0 (22.0%) | — | — | — | 624.0 (78.0% | — | — | — | 800 |
| 39 | 228.0 (28.5%) | — | — | — | 572.0 (71.5%) | — | — | — | 800 |
| 40 | 176.0 (22.0%) | — | — | — | 504.0 (63.0%) | 120.0 (15.0%) | — | — | 800 |
| 41 | 176.0 (22.0%) | — | 120.0 (15%) | — | 504.0 (63.0%) | — | — | — | 800 |
| 42 | 176.0 (22.0%) | 120.0 (15.0%) | — | — | 504.0 (63.0%) | — | — | — | 800 |
| 43 | 120.0 (15%) | 680.0 (85%) | — | — | — | — | — | — | 800 |
| 44 | 120.0 (15%) | 340.0 (42.5%) | — | — | 320.0 (40.0%) | — | — | 20.0 (2.5%) | 800 |
| 45 | 120.0 (15%) | — | — | 680.0 (85%) | — | — | — | — | 800 |
| 46 | 120.0 (15%) | — | 680.0 (85%) | — | — | — | — | — | 800 |
| 47 | 120.0 (15%) | — | 660.0 (82.5%) | — | — | — | — | 20.0 (2.5%) | 800 |
| 48 | 176.0 (22.0%) | 120.0 (15.0%) | — | — | 504.0 (63.0%) | — | — | — | 800 |
| 49 | 120.0 (15%) | — | — | 408.0 (51%) | 272.0 (34%) | — | — | — | 800 |
| 50 | 120.0 (15%) | — | — | 370.48 (46.31) | 246.88 (30.86%) | — | — | — | 800 |
| 51 | 120.0 (15%) | 140.0 (17.5%) | — | — | 520.0 (65.0%) | — | — | 20.0 (2.5%) | 800 |
| 52 | 182.65 (22.83%) | 97.36 (12.17%) | — | — | 520.0 (65.0%) | — | — | — | 800 |
| 53 | 182.65 (22.83%) | — | 97.36 (12.17%) | 208.0 (26%) | 312.0 (39%) | — | — | — | 800 |
| 54 | 120.0 (15%) | — | — | 204.0 (25.5%) | 476.0 (59.5%) | — | — | — | 800 |
| 55 | 182.65 (22.83%) | — | — | 185.21 (23.15%) | 432.15 (54.02%) | — | — | — | 800 |
| 56 | 182.65 (22.83%) | — | — | 185.21 (67.01%) | 81.28 (10.16%) | — | — | — | 800 |
| 59 | 120.0 (15%) | — | 320.0 (40%) | — | 340.0 (42.5%) | — | 20.0 (2.5%) | — | 800 |

Formulation numbers 50, 51 and 54 are preferred embodiments. As well, while a variety of solvents may be useful in the formulations presented in Table 3, preferred solvents may have the following characteristics: $C_4$-$C_{24}$ fatty acids and/or their glycerol-, propylene glycol-, polyethylene glycol-, sorbitan-mono-/diesters alone and in mixtures. Preferred fatty acids and esters are $C_8$-$C_{18}$, saturated and unsaturated. In addition, the solvents include, fatty acid esters with lower alcohols, such as ethyl oleate, ethyl linoleate, isopropyl myristate, isopropylpalmitate, isopropyloleate and isopropyllinoleate.

EXAMPLE

Figure 11:
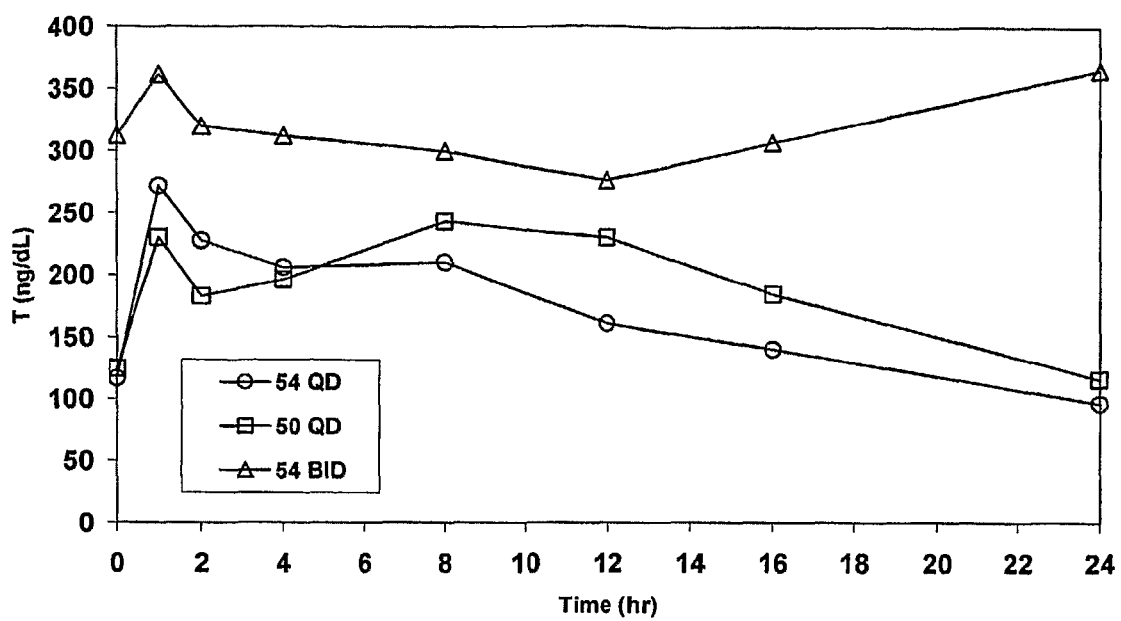
FIG. 11 provides the mean steady-state profile of treatment with three regimens for seven days.
Figure 12:
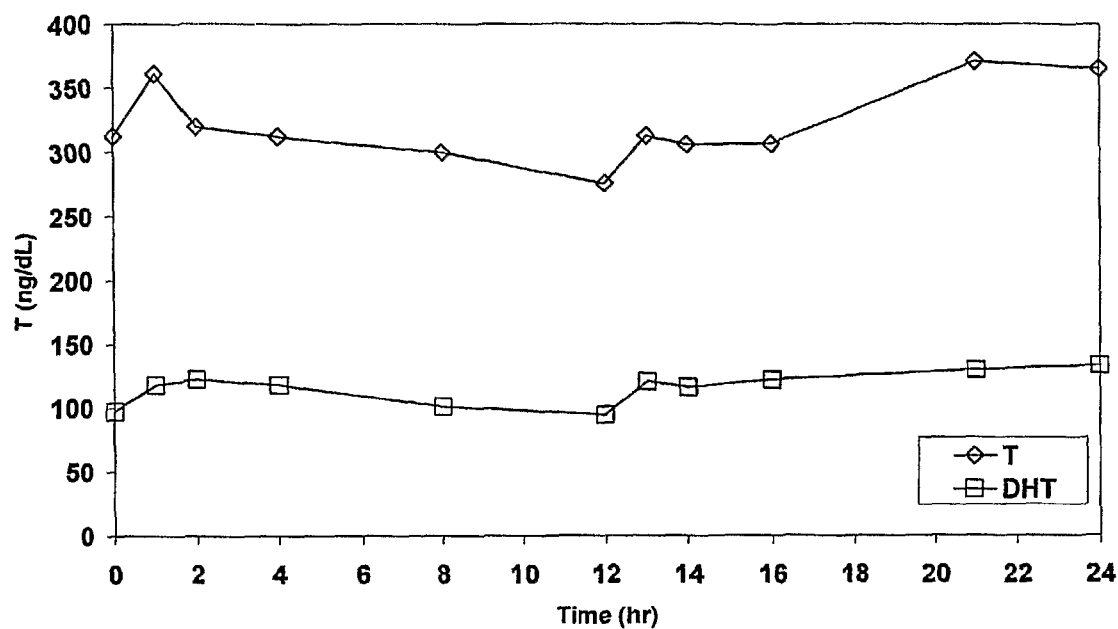
FIG. 12 shows the mean steady-state serum T and DHT Levels after seven days of BID administration of formulation 54.

Formulations 50 and 54 were administered to 6 patients; number 50 was administered once-daily ("QD") in the form of two capsules per dose (100 mg T equivalents/capsule) and number 54 was administered once- and twice-daily ("BID") in the form of three capsules per dose (66 mg T equivalents/capsule). The mean steady-state profiles after 7 days of treatment with one of the three, respective, regimens are shown in FIG. 11. The pharmacokinetic profile for formulation 54 BID was relatively uniform over the entire 24 hr period and had a trough of the mean profile about 70% of the peak of the mean profile. Additional data from formulation 54 include:
- Average serum T increase from baseline of 275 ng/dL
- Mean serum T levels at lower end of normal range, i.e., about 325 ng/dL.
- Relatively fast release ($T_{max}$ of about 1 hour)
- Estimated terminal half-life of T at steady-state of approximately 8-9 hours
- Consistent dose-related elevation in serum T baseline levels over the 7-day treatment period
- Average steady-state serum DHT level of 114 ng/dL (FIG. 12)

Figure 13:
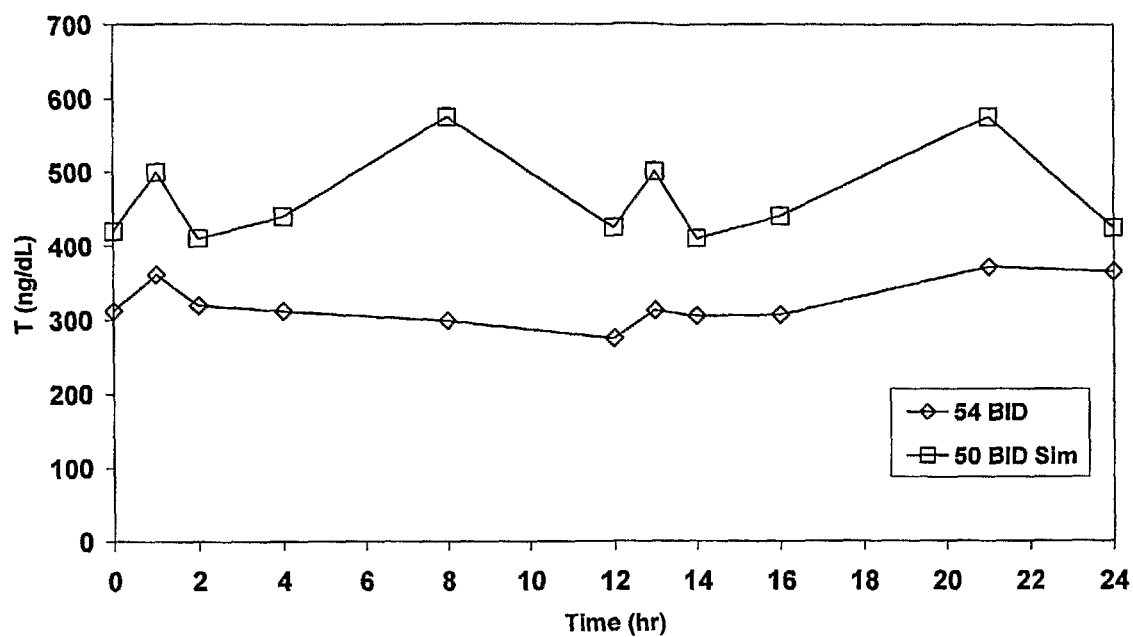
FIG. 13 provides a simulated mean steady-state profile of formulation 50 with respect to the observed profile for formulation 54 (both administered BID for seven days).

A simulation of the pharmacokinetic profile of formulation 50 administered BID was performed and compared to the observed profile for formulation 54 administered BID. The simulation predicts about a 384 ng/dL increase in $C_{avg}$ over the 24-hour period for formulation 50 over formulation 54 (FIG. 13).

In other embodiments of the present invention, methods and compositions for modulating (i.e., sustaining) the rate of available serum testosterone by incorporating component(s) that may biochemically modulate (1) TP absorption, (2) TP metabolism to T, and/or (3) metabolism of T to DHT. For example, the inclusion of medium to long chain fatty acid esters can enhance TP absorption. Without being held to or bound by theory, the present inventors believe that the use of effective amounts fatty acid esters, particularly palmitate esters such as ascorbyl-palmitate, retinyl-palmitate, sorbitan-palmitate and blends thereof may establish competition between said ester and TP for endogenous esterase activity. Indeed, it is believed that testosterone ester metabolism, generally, may be retarded with the administration of an effective amount of an ester of a medium or long chain fatty acid (e.g., esters of oleic acid, linoleic acid, linolenic acid, stearic acid, myristic acid, lauric acid, palmitic acid, capric or decanoic acid octanoic or caprylic acid, pelargonic acid, undecanoic acid, tridecanoic acid, pentadecanoic acid, and the branched chain, cyclic analogues of these acids). In this way, more TP may stave off hydrolysis in the gut and enter the blood stream. In other words, the fatty acid ester may competitively inhibit esterases that would otherwise metabolize TP. Table 4 provides effective amounts of inhibitors of testosterone ester metabolism. Examples of other esters or combinations thereof include botanical extracts or benign esters used as food additives (e.g., propylparben, octylacetate, and ethylacetate).

Other components that can modulate TP absorption include "natural" and synthetic inhibitors of 5α-reductase, which is present in enterocytes and catalyze the conversion of T to DHT. Complete or partial inhibition of this conversion may both increase and sustain increases serum levels of T after oral dosing with TP while concomitantly reducing serum DHT levels. Borage oil, which contains a significant amount of the 5α-reductase inhibitor gamma-linoleic acid (GLA), is an example of a "natural" modulator of TP metabolism. Other than within borage oil, of course, GLA could be directly added as a separate component of TP formulations described herein. Many natural inhibitors of 5α-reductase are known in the art (e.g., epigallocatechin gallate, a catechin derived primarily from green tea and saw palmetto extract from berries of the *Serenoa repens* species), all of which may be suitable in the present invention. Non-limiting examples of synthetic 5α-reductase inhibitors suitable in the present invention include finasteride and dutasteride.

In addition to 5α-reductase inhibitors, the present invention contemplates the use of inhibitors of T metabolism via other mechanisms. One such point of inhibition may be the cytochrome P450 isozyme CYP3A4 that is present in enterocytes and in liver cells and thus capable of metabolizing testosterone. Accordingly, formulations of the present invention, in some embodiments, include peppermint oil, which is known to contain factors capable of inhibiting CYP3A4.

Figure 14:
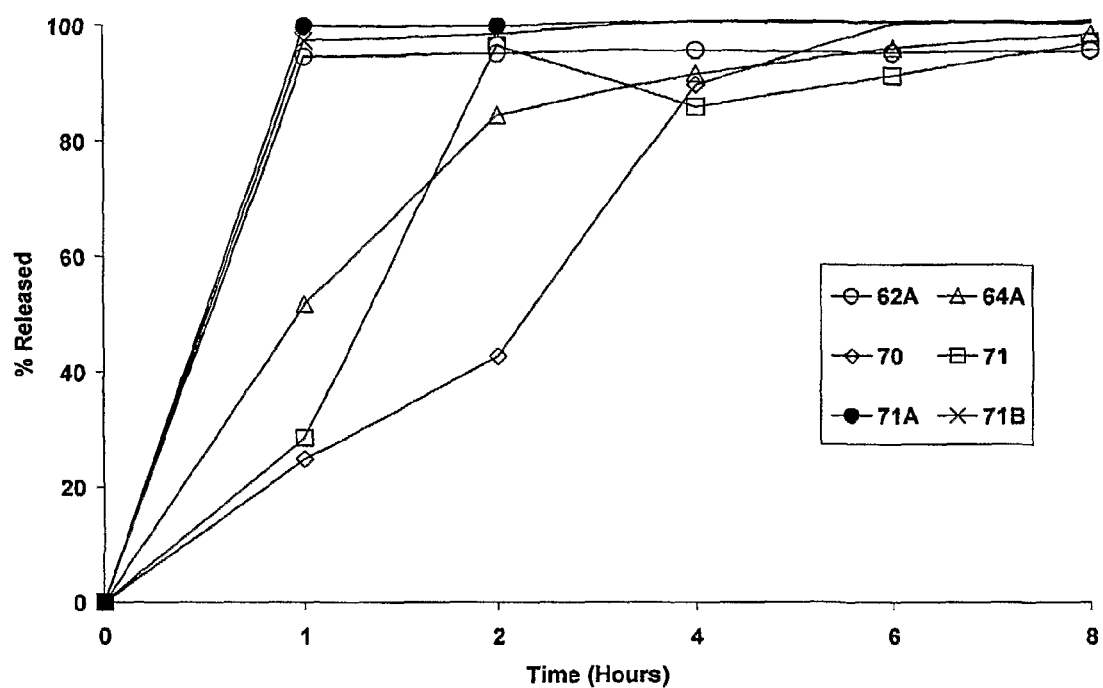
FIG. 14 shows representative in vitro dissolution profiles for various TP formulations in phosphate buffer (PBS)
Figure 15:
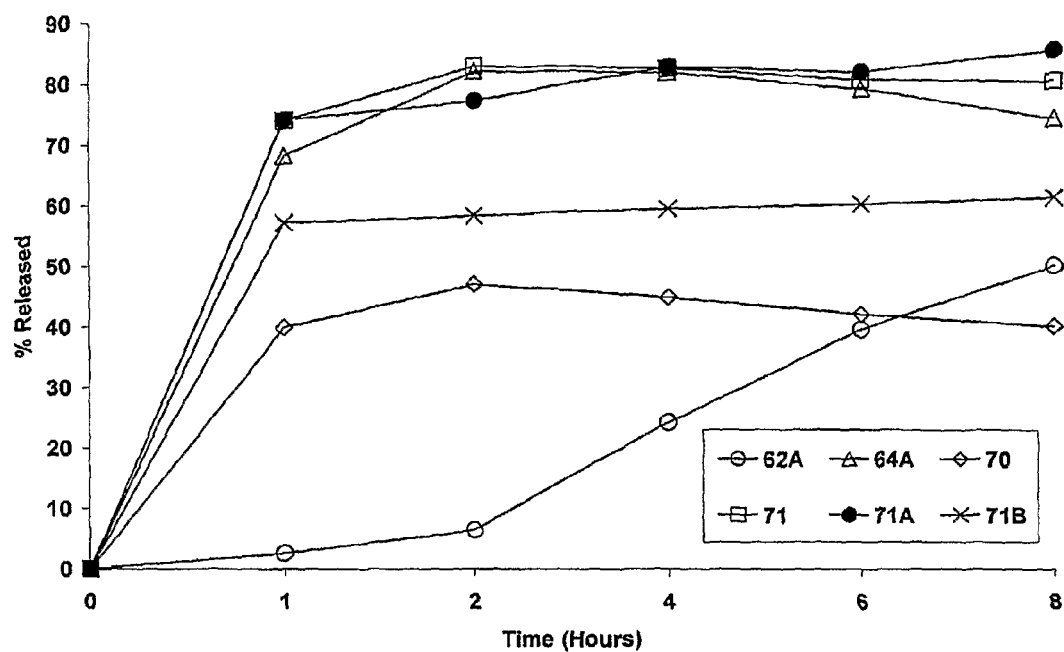
FIG. 15 shows representative in vitro dissolution profiles for various TP formulations in fed-state simulated intestinal fluid (FeSSIF).

Table 4 provides composition details of various TP formulations comprising ingredients to modulate TP absorption (i.e., ascorbyl-palmitate, borage oil and peppermint oil). FIGS. 14 and 15 show representative in vitro dissolution profiles for select TP formulations therein in either phosphate buffer (PBS) or fed-state simulated intestinal fluid (FeSSIF), respectively.

TABLE 4

| | Composition % w/w (mg/"00" capsule)[1] | | | | | | | | Fill |
| F. No. | TP | Ascorbyl-Palmitate | Cremophor RH40 | Cremophor EL | Oleic Acid | Peceol | Borage Oil | Peppermint Oil | Wt. (mg)[2] |
| --- | --- | --- | --- | --- | --- | --- | --- | --- | --- |
| 62 | 30.0 (240) | 2.5 (20) | — | — | 67.5 (540) | — | — | — | 800 |
| 62A | 15.0 (120) | 2.5 (20) | — | — | 82.5 (660) | — | — | — | 800 |
| 63 | 30.0 (240) | 5.0 (40) | — | — | 65.0 (520) | — | — | — | 800 |
| 63A | 22.9 (183) | 5.0 (40) | 12.2 (97) | — | 60.0 (480) | — | — | — | 800 |
| 64 | 15.0 | 15.0 | — | — | 70.0 | — | — | — | 800 |

TABLE 4-continued

| F. No. | TP | Ascorbyl-Palmitate | Cremophor RH40 | Cremophor EL | Oleic Acid | Peceol | Borage Oil | Peppermint Oil | Fill Wt. (mg)[2] |
|---|---|---|---|---|---|---|---|---|---|
|  | (120) | (120) |  |  | (560) |  |  |  |  |
| 64A | 15.0 | 10.0 | 25.0 | — | 50.0 | — | — | — | 800 |
|  | (120) | (80) | (200) |  | (400) |  |  |  |  |
| 65 | 22.9 | — | 25.0 | — | 52.0 | — | — | — | 800 |
|  | (183) |  | (200) |  | (417) |  |  |  |  |
| 66 | 15.0 | — | 42.5 | — | — | 42.5 | — | — | 800 |
|  | (120) |  | (340) |  |  | (340) |  |  |  |
| 67 | 15.0 | — | 30.0 | — | — | 55.0 | — | — | 800 |
|  | (120) |  | (240) |  |  | (440) |  |  |  |
| 68 | 22.9 | — | 20.0 | — | 45.0 | 12.0 | — | — | 800 |
|  | (183) |  | (160) |  | (360) | (96) |  |  |  |
| 69 | 22.9 | — | — | — | 53.0 | 19.0 | — | — | 800 |
|  | (183) |  |  |  | (424) | (152) |  |  |  |
| 70 | 22.9 | 10.0 | 25.0 | — | 22.1 | — | 10.0 | 10.0 | 800 |
|  | (183) | (80) | (200) |  | (177) |  | (80) | (80) |  |
| 70B | 22.9 | 2.5 | 20.0 | — | 39.7 | — | 10.0 | 5.0 | 800 |
|  | (183) | (20) | (160) |  | (318) |  | (80) | (40) |  |
| 71 | 15.0 | 10.0 | 25.0 | — | 30.0 | — | 10.0 | 10.0 | 800 |
|  | (120) | (80) | (200) |  | (240) |  | (80) | (80) |  |
| 71A | 10.0 | 2.5 | 20.0 | — | 52.5 | — | 10.0 | 5.0 | 800 |
|  | (80) | (20) | (160) |  | (420) |  | (80) | (40) |  |
| 71B | 15.0 | 2.5 | 20.0 | — | 47.5 | — | 10.0 | 5.0 | 800 |
|  | (120) | (20) | (160) |  | (380) |  | (80) | (40) |  |
| 72 | 15.0 | — | 60.0 | — | 25.0 | — | — | — | 800 |
|  | (120) |  | (480) |  | (200) |  |  |  |  |
| 73 | 15.0 | — | — | 60.0 | 25.0 | — | — | — | 800 |
|  | (120) |  |  | (480) | (200) |  |  |  |  |

[1] Milligram weights rounded to nearest whole number
[2] ±1 mg

In yet another embodiment of the present invention, drug delivery systems disclosed herein may also be suitable for ameliorating some of the side-effects of certain strategies for male contraception. For example, progestin-based male contraception substantially suppresses luteinizing hormone (LH) and follicle-stimulating hormone (FSH), and thereby suppresses spermatogenesis, resulting in clinical azoospermia (defined as less than about 1 million sperm/ml semen for 2 consecutive months). However, administration of progestins also has the undesirable side-effect of significantly reducing steady-state serum testosterone levels.

In such situations, for example, it may be preferable to provide preparations of progestin concomitantly with testosterone or a testosterone derivative (e.g., TP). More preferably, a pharmaceutical preparation according to the invention is provided, comprising progestin—in an amount sufficient to substantially suppress LH and FSH production—in combination with testosterone. In some embodiments, the pharmaceutical preparation is for once-daily, oral delivery.

Drug delivery systems, in one aspect of the present invention, afford the flexibility to achieve desirable pharmacokinetic profiles. Specifically, the formulations can be tailored to deliver medicament in a relatively early peak serum concentration ($T_{max}$) or one that appears later. See FIGS. 1, 3, 5 and 7 versus FIGS. 2, 4, 6 and 8, respectively. Similarly, the formulations may be tailored to have a relative steep or wide drop in drug serum concentration upon obtaining $T_{max}$. See FIGS. 1, 3, 5 and 7 versus FIGS. 2, 4, 6 and 8, respectively. Accordingly, pharmaceutical preparations of the instant invention may be administered once-daily, twice-daily, or in multiple doses per day, depending on, for example, patient preference and convenience.

One way in which the formulations may be modified to affect these changes is to calibrate the ratio of lipophilic surfactants. The magnitude and timing of the $T_{max}$, for example, can be affected by not only the type of lipids used, but also the ratios thereof. For example, to obtain a relatively early $T_{max}$, or fast release of the medicament from the delivery system, the concentration of the "controlled-release" lipophilic surfactant (e.g., Precirol) may be reduced relative to the concentration of the other lipophilic solvents (e.g., Labrafil M1944CS). On the other had, to achieve a delayed $T_{max}$, the percentage of "controlled-release" lipophilic surfactant in composition can be increased. FIGS. 9 and 10 show in vitro dissolution curves of TP from three formulations, respectively, in a phosphate buffered dissolution medium incorporating TritonX-100 as a surfactant in accordance with the present invention.

Without being bound by or limited to theory, it is believed that the inventive formulations described herein, in one aspect, enhance absorption of a medicament therein by the intestinal lymphatic system. In this way, drug delivery systems of the present invention can provide extended release formulations that can deliver testosterone into the serum over several hours. The serum half-life of testosterone in men is considered to be in the range of 10 to 100 minutes, with the upper range for testosterone administered in a form (i.e., TU) that favors lymphatic absorption. However, oral dosages of the present invention can be taken by a patient in need of testosterone therapy once every about twelve hours to maintain desirable levels of serum testosterone. In a more preferred embodiment, oral dosages are taken by a patient in need of testosterone therapy once every about twenty four hours. In general, "desirable" testosterone levels are those levels found in a human subject characterized as not having testosterone deficiency.

While the invention has been described in connection with specific embodiments thereof, it will be understood that it is capable of further modifications and this application is intended to cover any variations, uses, or alterations of the invention following. In general, the principles of the invention and including such departures from the present disclosure as come within known or customary practice within the art to which the invention pertains and as may be applied to the essential features hereinbefore set forth and as follows in the scope of the appended claims.

We claim:

1. A pharmaceutical composition suitable for oral administration to a mammalian subject, comprising:
   (a) 10-20 percent by weight of solubilized testosterone ester;
   (b) 5-20 percent by weight of hydrophilic surfactant;
   (c) 50-70 percent by weight of lipophilic surfactant; and
   (d) 10-15 percent by weight of digestible oil,
   which composition is free of ethanol and exhibits a percent (%) in vitro dissolution profile in phosphate buffered saline, which indicates release from the composition of substantially all of the solubilized testosterone ester within about 2 hours.

2. The pharmaceutical composition of claim 1, in which the testosterone ester is a short-chain ($C_2$-$C_6$) or a medium-chain ($C_7$-$C_{13}$) fatty acid ester.

3. The pharmaceutical composition of claim 2, in which the testosterone ester is a medium-chain fatty acid ester selected from the group consisting of testosterone cypionate, testosterone octanoate, testosterone enanthate, testosterone decanoate, and testosterone undecanoate.

4. The pharmaceutical composition of claim 3, in which the testosterone ester is testosterone undecanoate.

5. The pharmaceutical composition of claim 1, in which the hydrophilic surfactant exhibits an HLB of 10 to 45.

6. The pharmaceutical composition of claim 5, in which the hydrophilic surfactant is selected from the group consisting of polyoxyethylene sorbitan fatty acid esters, hydrogenated castor oil ethoxylates, PEG mono- and di-esters of palmitic and stearic acids, fatty acid ethoxylates, and combinations thereof.

7. The pharmaceutical composition of claim 6, in which the hydrophilic surfactant is a hydrogenated castor oil ethoxylate.

8. The pharmaceutical composition of claim 1, in which the lipophilic surfactant exhibits an HLB of less than 10.

9. The pharmaceutical composition of claim 8, in which the lipophilic surfactant exhibits an HLB of less than 5.

10. The pharmaceutical composition of claim 9, in which the lipophilic surfactant exhibits an HLB of 1 to 2.

11. The pharmaceutical composition of claim 8, in which the lipophilic surfactant exhibits an HLB of less than 5.

12. The pharmaceutical composition of claim 9, in which the lipophilic surfactant exhibits an HLB of 1 to 2.

13. The pharmaceutical composition of claim 12, in which the lipophilic surfactant is a fatty acid selected from the group consisting of octanoic acid, decanoic acid, undecanoic acid, lauric acid, myristic acid, palmitic acid, stearic acid, oleic acid, linoleic acid, and linolenic acid.

14. The pharmaceutical composition of claim 8, in which the lipophilic surfactant is a fatty acid selected from the group consisting of octanoic acid, decanoic acid, undecanoic acid, lauric acid, myristic acid, palmitic acid, stearic acid, oleic acid, linoleic acid, and linolenic acid.

15. The pharmaceutical composition of claim 1, in which the digestible oil is a vegetable oil selected from the group consisting of soybean oil, safflower seed oil, corn oil, olive oil, castor oil, cottonseed oil, arachis oil, sunflower seed oil, coconut oil, palm oil, rapeseed oil, evening primrose oil, grape seed oil, wheat germ oil, sesame oil, avocado oil, almond oil, borage oil, peppermint oil and apricot kernel oil.

16. The pharmaceutical composition of claim 1, which comprises one or more additional lipid-soluble therapeutic agents.

17. The pharmaceutical composition of claim 16, in which the one or more additional lipid-soluble therapeutic agents are selected from the group consisting of a synthetic progestin, an inhibitor of type-I and/or type II 5α-reductase, finasteride, dutasteride and combinations thereof.

18. The pharmaceutical composition of claim 16, in which the one or more additional lipid-soluble therapeutic agents comprises a second testosterone ester.

19. The pharmaceutical composition of claim 1 filled into a hard or soft gelatin capsule.

20. The pharmaceutical composition of claim 1, which exhibits a percent (%) in vitro dissolution profile in phosphate buffered saline, indicating release from the composition of substantially all of the solubilized testosterone ester within about 1 hour.

21. A pharmaceutical composition suitable for oral administration to a mammalian subject, comprising:
   (a) 10-20 percent by weight of solubilized testosterone undecanoate;
   (b) 5-20 percent by weight of a hydrogenated castor oil ethoxylate;
   (c) 50-70 percent by weight of oleic acid; and
   (d) 10-15 percent by weight of digestible oil,
   which composition is free of ethanol and exhibits a percent (%) in vitro dissolution profile in phosphate buffered saline, which indicates release from the composition of substantially all of the solubilized testosterone ester within about 2 hours.

22. A pharmaceutical composition suitable for oral administration to a mammalian subject, comprising:
   (a) 15-20 percent by weight of solubilized testosterone ester;
   (b) 5-20 percent by weight of hydrophilic surfactant;
   (c) 50-70 percent by weight of lipophilic surfactant; and
   (d) 10-15 percent by weight of digestible oil,
   which composition is free of ethanol and exhibits a percent (%) in vitro dissolution profile in phosphate buffered saline, which indicates release from the composition of substantially all of the solubilized testosterone ester within about 2 hours.

23. The pharmaceutical composition of claim 22, in which the testosterone ester is a short-chain ($C_2$-$C_6$) or a medium-chain ($C_7$-$C_{13}$) fatty acid ester.

24. The pharmaceutical composition of claim 23, in which the testosterone ester is a medium-chain fatty acid ester selected from the group consisting of testosterone cypionate, testosterone octanoate, testosterone enanthate, testosterone decanoate, and testosterone undecanoate.

25. The pharmaceutical composition of claim 24, in which the testosterone ester is testosterone undecanoate.

26. The pharmaceutical composition of claim 22, in which the hydrophilic surfactant exhibits an HLB of 10 to 45.

27. The pharmaceutical composition of claim 26, in which the hydrophilic surfactant is selected from the group consisting of polyoxyethylene sorbitan fatty acid esters, hydrogenated castor oil ethoxylates, PEG mono- and di-esters of palmitic and stearic acids, fatty acid ethoxylates, and combinations thereof.

28. The pharmaceutical composition of claim 27, in which the hydrophilic surfactant is a hydrogenated castor oil ethoxylate.

29. The pharmaceutical composition of claim 22, in which the lipophilic surfactant exhibits an HLB of less than 10.

30. The pharmaceutical composition of claim 22, in which the digestible oil is a vegetable oil selected from the group consisting of soybean oil, safflower seed oil, corn oil, olive oil, castor oil, cottonseed oil, arachis oil, sunflower seed oil, coconut oil, palm oil, rapeseed oil, evening primrose oil, grape seed oil, wheat germ oil, sesame oil, avocado oil, almond oil, borage oil, peppermint oil and apricot kernel oil.

31. The pharmaceutical composition of claim 22, which comprises one or more additional lipid-soluble therapeutic agents.

32. The pharmaceutical composition of claim 31, in which the one or more additional lipid-soluble therapeutic agents are selected from the group consisting of a synthetic progestin, an inhibitor of type-I and/or type II 5α-reductase, finasteride, dutasteride and combinations thereof.

33. The pharmaceutical composition of claim 32, in which the one or more additional lipid-soluble therapeutic agents comprises a second testosterone ester.

34. The pharmaceutical composition of claim 22 filled into a hard or soft gelatin capsule.

35. The pharmaceutical composition of claim 22, which exhibits a percent (%) in vitro dissolution profile in phosphate buffered saline, indicating release from the composition of substantially all of the solubilized testosterone ester within about 1 hour.

36. A pharmaceutical composition suitable for oral administration to a mammalian subject, comprising:
  (a) 15-20 percent by weight of solubilized testosterone undecanoate;
  (b) 5-20 percent by weight of a hydrogenated castor oil ethoxylate;
  (c) 50-70 percent by weight of oleic acid; and
  (d) 10-15 percent by weight of digestible oil,
which composition is free of ethanol and exhibits a percent (%) in vitro dissolution profile in phosphate buffered saline, which indicates release from the composition of substantially all of the solubilized testosterone ester within about 2 hours.

37. A pharmaceutical composition suitable for oral administration to a mammalian subject, comprising:
  (a) 15-20 percent by weight of solubilized testosterone ester;
  (b) 5-20 percent by weight of hydrophilic surfactant;
  (c) 50-70 percent by weight of a lipophilic surfactant which is a $C_{14}$-$C_{24}$ fatty acid; and
  (d) 10-15 percent by weight of digestible oil,
which composition exhibits a percent (%) in vitro dissolution profile in phosphate buffered saline, which indicates release from the composition of substantially all of the solubilized testosterone ester within about 2 hours.

38. The pharmaceutical composition of claim 37, in which the testosterone ester is a short-chain ($C_2$-$C_6$) or a medium-chain ($C_7$-$C_{13}$) fatty acid ester.

39. The pharmaceutical composition of claim 38, in which the testosterone ester is a medium-chain fatty acid ester selected from the group consisting of testosterone cypionate, testosterone octanoate, testosterone enanthate, testosterone decanoate, and testosterone undecanoate.

40. The pharmaceutical composition of claim 39, in which the testosterone ester is testosterone undecanoate.

41. The pharmaceutical composition of claim 37, in which the hydrophilic surfactant exhibits an HLB of 10 to 45.

42. The pharmaceutical composition of claim 41, in which the hydrophilic surfactant is selected from the group consisting of polyoxyethylene sorbitan fatty acid esters, hydrogenated castor oil ethoxylates, PEG mono- and di-esters of palmitic and stearic acids, fatty acid ethoxylates, and combinations thereof.

43. The pharmaceutical composition of claim 42, in which the hydrophilic surfactant is a hydrogenated castor oil ethoxylate.

44. The pharmaceutical composition of claim 37, in which the lipophilic surfactant exhibits an HLB of less than 10.

45. The pharmaceutical composition of claim 44, in which the lipophilic surfactant exhibits an HLB of less than 5.

46. The pharmaceutical composition of claim 45, in which the lipophilic surfactant exhibits an HLB of 1 to 2.

47. The pharmaceutical composition of claim 44, in which the lipophilic surfactant is selected from the group consisting of myristic acid, palmitic acid, stearic acid, oleic acid, linoleic acid, and linolenic acid.

48. The pharmaceutical composition of claim 37, in which the digestible oil is a vegetable oil selected from the group consisting of soybean oil, safflower seed oil, corn oil, olive oil, castor oil, cottonseed oil, arachis oil, sunflower seed oil, coconut oil, palm oil, rapeseed oil, evening primrose oil, grape seed oil, wheat germ oil, sesame oil, avocado oil, almond oil, borage oil, peppermint oil and apricot kernel oil.

49. The pharmaceutical composition of claim 37, which comprises one or more additional lipid-soluble therapeutic agents.

50. The pharmaceutical composition of claim 49, in which the one or more additional lipid-soluble therapeutic agents are selected from the group consisting of a synthetic progestin, an inhibitor of type-I and/or type II 5α-reductase, finasteride, dutasteride and combinations thereof.

51. The pharmaceutical composition of claim 50, in which the one or more additional lipid-soluble therapeutic agents comprises a second testosterone ester.

52. The pharmaceutical composition of claim 37 filled into a hard or soft gelatin capsule.

53. The pharmaceutical composition of claim 37, which exhibits a percent (%) in vitro dissolution profile in phosphate buffered saline, indicating release from the composition of substantially all of the solubilized testosterone ester within about 1 hour.

54. A pharmaceutical composition suitable for oral administration to a mammalian subject, comprising:
  (a) 15-20 percent by weight of solubilized testosterone undecanoate;
  (b) 5-20 percent by weight of a hydrogenated castor oil ethoxylate;
  (c) 50-70 percent by weight of oleic acid; and
  (d) 10-15 percent by weight of digestible oil,
which composition exhibits a percent (%) in vitro dissolution profile in phosphate buffered saline, which indicates release from the composition of substantially all of the solubilized testosterone ester within about 2 hours.

55. A method of alleviating symptoms of testosterone deficiency in a mammalian subject, comprising orally administering to a subject in need thereof an effective amount of a pharmaceutical composition according to claim 1, 2, 3, 16, 17, 9, 10, 32, 33, or 48.

56. The method of claim 55, in which the mammalian subject is a human male.

57. The method of claim 55, in which the mammalian subject is a human female.

58. The method of claim 55, in which an effective amount of the pharmaceutical composition is administered only once or twice daily.

59. The method of claim 55, which further comprises administering an amount of a synthetic progestin sufficient to substantially inhibit gonadotropin release in said mammalian subject.

* * * * *